(12) United States Patent
Agostino et al.

(10) Patent No.: US 8,632,611 B2
(45) Date of Patent: Jan. 21, 2014

(54) HAIR COLOURING METHODS AND COMPOSITIONS THEREOF

(71) Applicant: The Proctor & Gamble Company, Cincinnati, OH (US)

(72) Inventors: Elizabeth Hitchcock Agostino, Loveland, OH (US); Aideen Noelle Ripley, Cincinnati, OH (US); Stephen Robert Schofield, London (GB); Tracy Stephens, Albany, OH (US); Firoj Vohra, Mason, OH (US); Gabriele de Waal, GroB-Umstadt (DE); Graham John Myatt, Bracknell (GB); Andrei Sergeevich Bureiko, Cincinnati, OH (US); Brandon Scott Lane, Hamilton, OH (US); Jennifer Mary Marsh, Mason, OH (US); Jaime Beverly Vanderhorst, West Chester, OH (US); Simon Paul Godfrey, UXbridge (GB); Ozge Odman, Darmstadt (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 13/774,075

(22) Filed: Feb. 22, 2013

(65) Prior Publication Data

US 2013/0220358 A1    Aug. 29, 2013

Related U.S. Application Data

(60) Provisional application No. 61/602,637, filed on Feb. 24, 2012.

(51) Int. Cl.
*A61Q 5/10* (2006.01)

(52) U.S. Cl.
USPC ............... 8/405; 8/406; 8/408; 8/435; 8/485; 8/552; 132/202; 132/208

(58) Field of Classification Search
USPC ..................... 8/405, 406, 408, 435, 485, 552; 132/202, 208
See application file for complete search history.

(56) References Cited

U.S. PATENT DOCUMENTS

| 2,528,378 | A | 10/1950 | Mannheimer |
| 2,781,354 | A | 2/1957 | Mannheimer |
| 6,835,018 | B2 | 12/2004 | Miczewski et al. |
| 7,875,269 | B2 | 1/2011 | Bureiko |
| 2008/0178399 | A1 * | 7/2008 | Vena et al. ........... 8/407 |

* cited by examiner

*Primary Examiner* — Eisa Elhilo
(74) *Attorney, Agent, or Firm* — James T. Fondriest

(57) ABSTRACT

The present invention relates to a method for coloring hair wherein a hair coloring composition is applied to the hair roots. The hair coloring composition is then diluted with a dilutant component and the diluted hair coloring composition is applied to the hair lengths and tips.

19 Claims, No Drawings

HAIR COLOURING METHODS AND COMPOSITIONS THEREOF

FIELD OF THE INVENTION

The invention relates to a method of hair colouring, hair colouring composition and kits thereof.

BACKGROUND OF THE INVENTION

Consumers desiring to colour their hair typically have two options available namely to use a commercially available retail product or kit or use the services of a professional salon. The latter whilst providing a highly desirable colour outcome, is considerably more expensive than the retail option and thus not available to many consumers particularly those who colour regularly.

For consumers who have previously coloured their hair, the colour and condition of the hair is not homogenous along the entire length. The hair strands will comprise root virgin hair or new growth hair which has not been previously coloured and conversely at the tips hair which has experienced one or multiple hair colouring treatments. The tips of the hair typically are the most damaged portion of the hair and the colour will have changed over time dependant on the wash fade profile and number of types of hair colourant applied, amongst many relevant factors. The intermediate hair length is typically a medium between these two extreme conditions. As a consequence in the salon, for consumers who have previously coloured their hair, the salon stylists typically will colour the root virgin hair first with a specific composition to most effectively colour the hair to the desired end result. However, the remaining length of the hair and tips which has been previously coloured and may have undergone multiple colouring cycles is coloured with a separate and different composition to that applied at the roots. In this manner the salon stylist aims to provide a homogenous end colour result along the entire length of hair from root to tip independent of the variations of starting hair colour and condition along the hair length.

However, such a proposition is currently not available to consumers as a retail product, as it would add further to the complexity and cost and is thus not consumer desirable. Nevertheless, experienced home colour users continually strive to improve the overall colour outcome and indeed as outlined in the instruction packs of many retail products will often direct the consumer to apply the product to the virgin roots first prior to the application of the product along the entire length of hair. However these instructions are imprecise, often not followed, and the results achieved using this method are not comparable with those from a salon stylist. Not only is the overall colour result not as homogenous as that provided by a salon stylist, and may result in over deposition of colour and over bleaching or brassiness, but the rheology of the product also does not necessarily easily allow specific application at the root line as well as easy pull through the remaining length of hair, whilst ensuring no dripping, and good adhesion to the roots during root application. Alternative products on the retail market have been designed to be used only on the roots to address root growth. However these are not entirely satisfactory and a root touch up line may be clearly identifiable. Moreover these products do not remove the need for a separate colouring step for the remaining hair length.

Thus, there still exists a need to provide a retail colour system for use on roots and the entire hair length, without the need for providing and preparing two separate compositions to provide similar results as those associated with professional salon stylists and improved results versus current retail executions.

SUMMARY OF THE INVENTION

The present invention relates to a method for colouring hair comprising the steps of:
 i) mixing a developer component with a dye component to obtain a non-diluted hair colouring composition, wherein the developer component comprises an oxidizing agent and the dye component comprises at least one oxidative dye precursor and/or an alkalising agent;
 ii) applying a first portion of the non-diluted hair colouring composition obtained in step i) to the hair, preferably the hair roots and retaining a second portion of the non-diluted hair colouring composition obtained in step i);
 iii) mixing the second portion with a dilutant component comprising water and optionally at least one active component at a mixing ratio of 4:1 to 1:2 to obtain a diluted hair colouring composition;
 iv) applying the diluted hair colouring composition to the hair, preferably the hair lengths and tips
 v) rinsing the hair.

The present invention also relates to a hair colouring kit comprising a developer component comprising an oxidizing agent, a dye component comprising at least one oxidative dye precursor and/or an alkalising agent and a dilutant component comprising water and optionally at least one active component.

Furthermore, the present invention also relates to a hair colouring composition comprising a developer component comprising an oxidizing agent, and a dye component comprising at least one oxidative dye precursor and/or an alkalising agent, and a dilutant component comprising water and optionally at least one active component, wherein the hair colouring composition is obtainable by:
 i) Mixing the developer component and the dye component, wherein after mixing the developer component and the dye component, a first portion of the composition is applied to the hair, preferably the hair roots and a second portion of the composition is retained, and
 ii) Mixing the second portion of the composition with the dilutant component at a mixing ratio of 4:1 to 1:2.

DETAILED DESCRIPTION OF THE INVENTION

While the specification concludes with claims, which particularly point out and distinctly claim the invention, it is believed the present invention will be better understood from the following description.

As used herein the term "hair" to be treated may be "living" i.e. on a living body or may be "non-living" i.e. in a wig, hairpiece or other aggregation of non-living keratinous fibres. Mammalian, preferably human hair is preferred. However wool, fur and other keratin containing fibres are suitable substrates for the compositions according to the present invention. The terms "root", "hair roots", "root hair line" and "virgin hair" all refer to hair which has not been previously treated with a hair colouring composition.

In the preferred embodiment according to the present invention, the hair colouring compositions are applied to hair which has already been previously coloured with hair colouring compositions. In such a case, the terms "root", "hair roots", "root hair line" and "virgin hair" all refer to the portion of hair having grown, since the last hair colouration, said portion of hair being virgin, i.e. naturally-coloured and the terms "hair lengths and tips" refer to the remaining portion of hair having been already previously coloured.

All percentages are by weight of the total composition unless specifically stated otherwise. All ratios are weight ratios unless specifically stated otherwise.

Method for Colouring Hair

The present invention relates to a method for colouring hair as stated hereinbefore.

The first portion of the non-diluted hair colouring composition is preferably applied to the hair roots and the diluted hair colouring composition is preferably applied to the hair lengths and tips.

Natural hair typically goes from darker to lighter when moving from the roots to the tips. The inventors have surprisingly found that by carrying out a method for colouring hair according to the present invention it is possible to preserve a more natural root-to-tip transition. In addition, the hair is not a flat block color, but shows more of the natural variation of tones in the hair as a diluted colorant is applied to the lengths. Whilst not being bound by theory it is believed that mixing the developer component with the dye component to obtain a non-diluted composition and applying a first portion of the non-diluted composition directly onto the root virgin hair, delivers an effective composition to both lighten and colour previously uncoloured hair to the desired level. However, retaining a second portion of this non-diluted composition and mixing it with a dilutant component thereto provides a resultant diluted composition which reduces the overall effective lightening and colouring capacity of the non-diluted composition which can then be applied to the remaining pre-coloured hair length which requires less lightening and dye deposition in order to deliver a colour result similar to that resulting from the application of the first portion of the non-diluted composition applied to the roots. Whilst not being bound by theory it is believed that the use of a dilutant component with the second portion of the non-diluted composition reduces the concentration of actives species such as dye precursors, oxidizing agent such as hydrogen peroxide and alkalising agents if present before the dye formation process has completed thereby still enabling penetration of the dyes species into the hair shaft to provide permanent hair colour.

In step i) of the method, the developer component may be mixed with the dye component at a mixing ratio of 2:1 to 1:2, preferably 1:1.

In step ii) of the method, from 90 to 10%, preferably from 80 to 50%, more preferably from 75 to 55%, even more preferably from 75 to 60% by weight of the non-diluted hair colouring composition may be applied as a first portion to the hair roots.

The method according to the present invention may further comprise the step of waiting for a time period $T_1$ which is performed between steps ii) and iii) and/or the step of waiting for a time period $T_2$ which is performed between steps iv) and v), wherein:

a. $0.15 < \left(\frac{T_2}{T_1 + T_2}\right) \times \left(1 - \frac{b}{a+b}\right) < 0.30$ for hair which are coloured with non-vibrant hair shades such as blonde, brown or black hair shades or b. $0.55 < \left(\frac{T_2}{T_1 + T_2}\right) \times \left(1 - \frac{b}{a+b}\right) < 0.75$ for hair which are coloured with more vibrant, more tonal shades, such as red, violet, copper, wherein a and b are respectively the weight of the second portion of the non-diluted hair colouring composition and the weight of dilutant component which are mixed together in step iii).

If these values are met, a homogenous end colour result may be provided along the entire length of hair from root to tip.

The method may further comprise the step of waiting for a time period of from 10 min to 40 min, preferably from 15 min to 30 min, even more preferably 20 min, which is performed between steps ii) and iii), and the step of waiting for a time period of from 5 min to 20 min, preferably 10 min, which is performed between steps iv) and v). Such an embodiment may be used for colouring hair with non-tonal hair shades such as blonde, brown or black hair shades. Alternatively, step iii) may be performed immediately after step ii) and the method may further comprise the step of waiting for a time period of from 5 min to 40 min, preferably 20 min to 40 min, more preferably 30 min, which is performed between steps iv) and v). Such an embodiment may be used for colouring hair with more vibrant, tonal shades, such as red, violet, copper.

The second portion of the non-diluted hair colouring composition is preferably mixed with the dilutant component at a mixing ratio of 2:1 to 1:2, preferably 2:1 to obtain the diluted hair colouring composition.

In step v) of the method, the hair may be rinsed with water and/or shampoo. After rinsing, they may be further dried and styled as usual. A conditioner component may be applied to the hair after rinsing, preferably prior to drying and styling.

The developer component may comprise from 1 to 20% by weight of the oxidizing agent, the dye component may comprise from 0.01% to 10% by weight of the oxidative dye precursor and/or from 0.1% to 10% by weight of the alkalising agent, and the dilutant component may comprise up to 99% by weight of water and up to 25% by weight of at least one active component selected from surfactants, conditioning agents, polymers, and mixtures thereof.

The volume of developer component used in step i) of the method may be from 10 mL to 120 mL, preferably 40 mL to 70 mL, more preferably 55 mL to 65 mL, the volume of dye component used in step i) of the method may be from 10 mL to 120 mL, preferably 40 mL to 70 mL, more preferably 55 mL to 65 mL and the volume of dilutant component used in step iii) of the method may be from 10 mL to 70 mL, preferably 15 mL to 30 mL, more preferably 20 mL to 25 mL.

Hair Colouring Composition

Oxidizing Agent

The non-diluted and diluted hair colouring compositions of the present invention comprise a developer component comprising an oxidizing agent. The oxidizing agent is present in an amount sufficient to bleach the melanin pigment in the hair and/or oxidize dye precursors. Typically, such an amount ranges from 1% to 20%, or from 3% to 15%, or from 6% to 12% by weight of the developer component. Inorganic peroxygen materials capable of yielding hydrogen peroxide in an aqueous medium are suitable and include, but are not limited to: hydrogen peroxide; inorganic alkali metal peroxides (e.g. sodium periodate and sodium peroxide); organic peroxides (e.g. urea peroxide, melamine peroxide); inorganic perhydrate salt bleaching compounds (e.g. alkali metal salts of perborates, percarbonates, perphosphates, persilicates, and persulphates, in some embodiments, sodium salts thereof), which may be incorporated as monohydrates, tetrahydrates, etc.; alkali metal bromates; enzymes; and mixtures thereof. Mixtures of two or more oxidizing agents may be used, for example hydrogen peroxide and sodium persulphate. The oxidizing agents may be provided in solution or as a powder which is dissolved prior to use. This is a preferred embodiment for persulphate based oxidizing agents. The oxidizing agent may be hydrogen peroxide. The non-diluted and diluted hair colouring compositions of the invention may comprise air oxidation or auto oxidation hair colorants. In these compositions, the dyes are oxidized by atmospheric oxygen.

Hair Dyes

The non-diluted and diluted hair colouring compositions of the present invention comprise a dye component comprising at least one oxidative dye precursor and/or an alkalizing agent. Oxidative dye precursors are usually classified either as primary intermediates (also known as developers) or couplers (also known as secondary intermediates). Various couplers may be used with primary intermediates in order to obtain different shades. Oxidative dye precursors may be free bases or the cosmetically acceptable salts thereof.

Typically, the non-diluted and/or the diluted compositions may comprise a total amount of oxidative dye precursors ranging up to 12%, alternatively from 0.1% to 10%, alternatively from 0.3% to about 8%, alternatively from 0.5% to about 6%, by weight of the total composition.

Suitable primary intermediates include, but are not limited to: toluene-2,5-diamine, p-phenylenediamine, N-phenyl-p-phenylenediamine, N,N-bis(2-hydroxyethyl)-p-phenylenediamine, 2-hydroxyethyl-p-phenylenediamine, hydroxypropyl-bis-(N-hydroxyethyl-p-phenylenediamine), 2-methoxymethyl-p-phenylenediamine, 2-(1,2-dihydroxyethyl)-p-phenylenediamine, 2,2'-(2-(4-aminophenylamino)ethylazanediyl)diethanol, 2-(2,5-diamino-4-methoxyphenyl)propane-1,3-diol, 2-(7-amino-2H-benzo[b][1,4]oxazin-4(3H)-yl)ethanol, 2-chloro-p-phenylenediamine, p-aminophenol, p-(methylamino)phenol, 4-amino-m-cresol, 6-amino-m-cresol, 5-ethyl-o-aminophenol, 2-methoxy-p-phenylenediamine, 2,2'-methylenebis-4-aminophenol, 2,4,5,6-tetraminopyrimidine, 2,5,6-triamino-4-pyrimidinol, 1-hydroxyethyl-4,5-diaminopyrazole sulfate, 4,5-diamino-1-methylpyrazole, 4,5-diamino-1-ethylpyrazole, 4,5-diamino-1-isopropylpyrazole, 4,5-diamino-1-butylpyrazole, 4,5-diamino-1-pentylpyrazole, 4,5-diamino-1-benzylpyrazole, 2,3-diamino-6,7-dihydropyrazolo[1,2-a]pyrazol-1 (5H)-one dimethosulfonate, 4,5-diamino-1-hexylpyrazole, 4,5-diamino-1-heptylpyrazole, methoxymethyl-1,4-diaminobenzene, N,N-bis(2-hydroxyethyl)-N-(4-aminophenyl)-1,2-diaminothane, salts thereof and mixtures thereof.

Suitable couplers include, but are not limited to: resorcinol, 4-chlororesorcinol, 2-chlororesorcinol, 2-methylresorcinol, 4,6-dichlorobenzene-1,3-diol, 2,4-dimethylbenzene-1,3-diol, m-aminophenol, 4-amino-2-hydroxytoluene, 2-methyl-5-hydroxyethylaminophenol, 3-amino-2,6-dimethylphenol, 3-amino-2,4-dichlorophenol, 5-amino-6-chloro-o-cresol, 5-amino-4-chloro-o-cresol, 6-hydroxybenzomorpholine, 2-amino-5-ethylphenol, 2-amino-5-phenylphenol, 2-amino-5-methylphenol, 2-amino-6-methylphenol, 2-amino-5-ethoxyphenol, 5-methyl-2-(methylamino)phenol, 2,4-diaminophenoxyethanol, 2-amino-4-hydroxyethylaminoanisole, 1,3-bis-(2,4-diaminophenoxy)-propane, 2,2'-(2-methyl-1,3-phenylene)bis(azanediyl)diethanol, benzene-1,3-diamine, 2,2'-(4,6-diamino-1,3-phenylene)bis(oxy)diethanol, 3-(pyrrolidin-1-yl)aniline, 1-(3-(dimethylamino)phenyl)urea, 1-(3-aminophenyl)urea, 1-naphthol, 2-methyl-1-naphthol, 1,5-naphthalenediol, 2,7-naphthalenediol or 1-acetoxy-2-methylnaphthalene, 4-chloro-2-methylnaphthalen-1-ol, 4-methoxy-2-methylnaphthalen-1-ol, 2,6-dihydroxy-3,4-dimethylpyridine, 2,6-dimethoxy-3,5-pyridinediamine, 3-amino-2-methylamino-6-methoxypyridine, 2-amino-3-hydroxypyridine, 2,6-diaminopyridine, pyridine-2,6-diol, 5,6-dihydroxyindole, 6-hydroxyindole, 5,6-dihydroxyindoline, 3-methyl-1-phenyl-1H-pyrazol-5(4H)-one, 1,2,4-trihydroxybenzene, 2-(benzo[d][1,3]dioxol-5-ylamino)ethanol (also known as hydroxyethyl-3,4-methylenedioxyaniline), and mixtures thereof.

The primary intermediates and couplers are usually incorporated into the dye component.

Alkalizing Agent

The dye component of the non-diluted and diluted hair colouring compositions may optionally comprise an alkalizing agent, preferably a source of ammonium ions and/or ammonia Alkalizing agent may include alkanolamines, for example monoethanolamine, diethanolamine, triethanolamine, monopropanolamine, dipropanolamine, tripropanolamine, 2-amino-2-methyl-1,3-propanediol, 2-amino-2-methyl-1-propanol, and 2-amino-2-hydroxymethyl-1,3-propanediol; guanidium salts; and alkali-metal and ammonium hydroxides and carbonates, such as sodium hydroxide and ammonium carbonate; and mixtures thereof. A preferred alkalizing agent is monoethanolamine. Particularly, preferred alkalizing agents are those which provide a source of ammonium ions. Any source of ammonium ions is suitable for use herein. Preferred sources include ammonium chloride, ammonium sulphate, ammonium nitrate, ammonium phosphate, ammonium acetate, ammonium carbonate, ammonium hydrogen carbonate, ammonium carbamate, ammonium hydroxide, ammonium percarbonate salts, ammonia and mixtures thereof. Particularly preferred are ammonium carbonate, ammonium carbamate, ammonia, ammonium hydroxide and mixtures thereof. The non-diluted and/or diluted hair colouring compositions of the present invention may comprise from 0.1% to 10%, or from 0.5% to 5%, or from 1% to 3% by weight of an alkalizing agent, preferably ammonium ions. Preferably, if present, the ammonium ions and carbonate ions are present in the hair colouring composition at a weight ratio of from 3:1 to 1:10, preferably 2:1 to 1:5.

The dye component may comprise from 0.1% to 5%, or from 0.2% to 3%, or from 0.5% to 2% by weight of an alkalizing agent.

Dilutant Component

The non-diluted hair colouring composition of the present invention comprise a dilutant component. The dilutant component comprises water and optionally at least one active component. The active component(s) may be selected from, surfactants, polymers, conditioning actives, solvents, C6 to C30 fatty alcohols, thickeners and mixtures thereof, preferably surfactants, polymers, conditioning agents and mixtures thereof as described hereinafter. Preferably, the dilutant component may comprise up to 99%, or up to 90%, or up to 85% by weight of water. Preferably, the dilutant component may comprise up to 25%, or from 1% to 20%, or from 5% to 20% by weight of the active component(s). Whilst not being bound by theory it is believed that the dilutant component acts to dilute the concentration of the second portion of the non-diluted hair colouring composition in particular the concentration of oxidizing agent and oxidative dye precursors and alkalising agent if present, to thereby reduce the overall effectiveness of the provision of lightening and colour to the hair.

Composition Components

The non-diluted and diluted hair colouring compositions may further comprise additional components, effective for use in oxidative dye compositions, including but not limited to: solvents; direct dyes; radical scavengers; thickeners and or rheology modifiers; chelants; pH modifiers and buffering agents; carbonate ion sources; peroxymonocarbonate ion sources; surfactants; polymers; fragrances; enzymes; dispersing agents; peroxide stabilizing agents; antioxidants; natural ingredients, e.g. proteins and protein derivatives, and plant extracts; conditioning agents; ceramides, preserving agents; and opacifiers and pearling agents (such as titanium dioxide and mica). These components may be comprised in the developer component, the dye component, the dilutant component or any combination thereof. Some adjuvants referred to above, but not specifically described below, which are suitable are listed in the International Cosmetics Ingredient Dictionary and Handbook, (8th ed.; The Cosmetics, Toiletry, and Fragrance Association). Particularly, vol. 2, sections 3 (Chemical Classes) and 4 (Functions) are useful in identifying specific adjuvants to achieve a particular purpose or multipurpose.

Direct Dyes

The non-diluted and diluted hair colouring compositions may comprise compatible direct dyes in an amount sufficient to provide colouring, particularly with regard to intensity. Typically, such an amount will range from 0.05% to 4%, by weight of the non-diluted or diluted hair colouring composition. Suitable direct dyes include but are not limited to: Acid Yellow 1; Acid Orange 3; Disperse Red 17; Basic Brown 17; Acid Black 52; Acid Black 1; Disperse Violet 4; 4-nitro-o-phenylenediamine; 2-nitro-p-phenylenediamine; Picramic Acid; HC Red No. 13; 1,4-bis-(2'-hydroxyethyl)-amino-2-nitrobenzene; HC Yellow No. 5; HC Red No. 7; HC Blue No. 2; HC Yellow No. 4; HC Yellow No. 2; HC Orange No. 1; HC Red No. 1; 2-chloro-5-nitro-N-hydroxyethyl-p-phenylenediamine; HC Red No. 3; 4-amino-3-nitrophenol; 2-hydroxyethylamino-5-nitroanisole; 3-nitro-p-hydroxyethylaminophenol; 2-amino-3-nitrophenol; 6-nitro-o-toluidine; 3-methylamino-4-nitrophenoxyethanol; 2-nitro-5-glyceryl-methylaniline; HC Yellow No. 11; HC Violet No. 1; HC Orange No. 2; HC Orange No. 3; HC Yellow No. 9; 4-nitro-phenylaminoethylurea; HC Red No. 10; HC Red No. 11; 2-hydroxyethyl picramic acid; HC Blue No. 12; HC Yellow No. 6; hydroxyethyl-2-nitro-p-toluidine; HC Yellow No. 12; HC Blue No. 10; HC Yellow No. 7; HC Yellow No. 10; HC Blue No. 9; N-ethyl-3-nitro PABA; 4-amino-2-nitrophenyl-amine-2'-carboxylic acid; 2-chloro-6-ethylamino-4-nitrophenol; 6-nitro-2,5-pyridinediamine; HC Violet No. 2; 2-amino-6-chloro-4-nitrophenol; 4-hydroxypropylamino-3-nitrophenol; HC Yellow No. 13; 1,2,3,4-tetrahydro-6-nitro-chinoxalin; HC Red No. 14; HC Yellow No. 15; HC Yellow No. 14; 3-amino-6-methylamino-2-nitropyridine; 2,6-diamino-3-((pyridine-3-yl)azo)pyridine; Basic Red No. 118; Basic Orange No. 69; N-(2-nitro-4-aminophenyl)-allylamine; 4-[(4-amino-3-methylphenyl)(4-imino-3-methyl-2,5-cyclohexadien-1-ylidene)methyl]-2-methyl-benzeneamine-hydrochloride; 2-[[4-(dimethyl-amino)phenyl]azo]-1,3-dimethyl-1H-imidazolium chloride; 1-methyl-4-[(methylphenyl-hydrazono)methyl]-pyridinium, methyl sulfate; 2-[(4-aminophenyl)azo]-1,3-dimethyl-1H-imidazolium chloride; Basic Red 22; Basic Red 76; Basic Brown 16; Basic Yellow 57; 7-(2',4'-dimethyl-5'-sulfophenylazo)-5-sulfo-8-hydroxynaphthalene; Acid Orange 7; Acid Red 33; 1-(3'-nitro-5'-sulfo-6'-oxophenylazo)-oxo-naphthalene chromium complex; Acid Yellow 23; Acid Blue 9; Basic Violet 14; Basic Blue 7; Basic Blue 26; sodium salt of mixture of mono- & disulfonic acids (mainly the latter) of quinophthlanone or 2-quinolylindandione; Basic Red 2; Basic Blue 99; Disperse Red 15; Acid Violet 43; Disperse Violet 1; Acid Blue 62; Pigment Blue 15; Acid Black 132; Basic Yellow 29; Disperse Black 9; 1-(N-methylmorpholinium-propylamino)-4-hydroxy-anthraquinone methylsulfate; HC Blue No. 8; HC Red No. 8; HC Green No. 1; HC Red No. 9; 2-hydroxy-1,4-naphthoquinone; Acid Blue 199; Acid Blue 25; Acid Red 4; Henna Red; Indigo; Cochenille; HC Blue No. 14; Disperse Blue 23; Disperse Blue 3; Disperse Blue 377; Basic Red 51; Basic Orange 31; Basic Yellow 87; and mixtures thereof. Preferred direct dyes include but are not limited to: Disperse Black 9; HC Yellow 2; HC Yellow 4; HC Yellow 15; 4-nitro-o-phenylenediamine; 2-amino-6-chloro-4-nitrophenol; HC Red 3; Disperse Violet 1; HC Blue 2; Disperse Blue 3; Disperse Blue 377; Basic Red 51; Basic Orange 31; Basic Yellow 87; and mixtures thereof.

pH Modifiers and Buffering Agents

The non-diluted and diluted hair colouring compositions of the present invention may have a pH of from 12 to 7.5, or from 11 to 8.4, or from 10 to 8.5. They may further comprise a pH modifier and/or buffering agent in an amount that is sufficiently effective to adjust the pH of the composition to fall within a range from 3 to 13, or from 7.5 to 12, or from 8.5 to 9.5 in some embodiments particularly those comprising a source of carbonate ions. Preferably the pH modifier or buffering agent is comprised in the dye component.

Suitable pH modifiers and/or buffering agents for use herein include, but are not limited to: ammonia, alkanolamides such as monoethanolamine, diethanolamine, triethanolamine, monopropanolamine, dipropanolamine, tripropanolamine, tripropanolamine, 2-amino-2-methyl-1-propanol, and 2-amino-2-hydroxymethyl-1,3-propandiol and guanidium salts, alkali metal and ammonium hydroxides and carbonates; in some embodiments, sodium hydroxide and ammonium carbonate, and acidulents such as inorganic and inorganic acids, e.g., phosphoric acid, acetic acid, ascorbic acid, citric acid or tartaric acid, hydrochloric acid, and mixtures thereof.

Chelants

The non-diluted and diluted hair colouring compositions of the present invention may contain a chelant (or "chelating agent" or "sequestering agent" or "sequestrant") or salt thereof. The presence of redox metals such as copper, iron, and calcium in tap water used by consumers, though only present at low levels of 5 to 100 ppm and, for calcium, 4000 to 10000 ppm, may effect the color chemistry of oxidative hair dyes. The presence of chelants may limit this effect. The term "salts thereof" means all salts comprising the same functional structure as the chelant they are referring to and includes alkali metal, alkaline earth, ammonium, substituted ammonium salts (e.g., monoethanolammonium, diethanolammonium, triethanolammonium), in particular all sodium, potassium or ammonium salts. The non-diluted and/or diluted hair colouring compositions may comprise from 0.01% to 5%, or from 0.25% to 3%, or from 0.5% to 1% by weight of chelant, salts thereof, derivatives thereof, or mixtures thereof. The chelant may be present in the developer component, the dye component, the dilutant component or any combination thereof.

Chelants are well known in the art and a non-exhaustive list thereof can be found in A E Martell & R M Smith, Critical Stability Constants, Vol. 1, Plenum Press, New York & London (1974) and A E Martell & R D Hancock, Metal Complexes in Aqueous Solution, Plenum Press, New York & London (1996), both incorporated herein by reference. Suitable chelants for use herein are carboxylic acids (in particular aminocarboxylic acids), phosphonic acids (in particular aminophosphonic acids) and polyphosphoric acids (e.g., linear polyphosphoric acids), and the salts thereof.

Aminocarboxylic acid chelants for use herein have at least one carboxylic acid moiety (—COOH) and at least one nitrogen atom. Examples of aminocarboxylic acid chelants suitable for use herein include diethylenetriamine pentaacetic acid (DTPA), ethylenediamine disuccinic acid (EDDS), ethylenediamine diglutaric acid (EDGA), 2-hydroxypropylenediamine disuccinic acid (HPDS), glycinamide-N,N'-disuccinic acid (GADS), ethylenediamine-N—N'-diglutaric acid (EDDG), 2-hydroxypropylenediamine-N—N'-disuccinic acid (HPDDS), ethylenediaminetetraacetic acid (EDTA), ethylenedicysteic acid (EDC), EDDHA (ethylenediamine-N—N'-bis(ortho-hydroxyphenyl acetic acid)), diaminoalkyldi(sulfosuccinic acids) (DDS), N,N'-bis(2-hydroxybenzyl) ethylenediamine-N,N'-diacetic acid (HBED) and salts thereof and mixtures thereof.

Other suitable aminocarboxylic type chelants for use herein are iminodiacetic acid derivatives such as N-2-hydroxyethyl N,N diacetic acid or glyceryl imino diacetic acid, iminodiacetic acid-N-2-hydroxypropyl sulfonic acid and aspartic acid N-carboxymethyl N-2-hydroxypropyl-3-sulfonic acid, β-alanine-N,N'-diacetic acid, aspartic acid-N,N'-diacetic acid, aspartic acid-N-monoacetic acid and iminodisuccinic acid chelants, ethanoldiglycine acid, and salts thereof and mixtures thereof. Dipicolinic acid and 2-phosphonobutane-1,2,4-tricarboxylic acid are also suitable. Preferred for use herein is ethylenediamine-N,N'-disuccinic acid (EDDS), and salts thereof.

Amino-phosphonic acid type chelants suitable for use herein are defined as chelants comprising an amino-phosphonic acid moiety (—$PO_3H_2$) or its derivative —$PO_3R_2$ wherein $R_2$ is a $C_1$ to $C_6$ alkyl or aryl radical and salts thereof.

Suitable amino-phosphonic acid type chelants for use herein are aminotri-(1-ethylphosphonic acid), ethylenediaminetetra-(1-ethylphosphonic acid), aminotri-(1-propylphosphonic acid), and aminotri-(isopropylphosphonic acid). Preferred chelants for use herein are aminotri-(methylenephosphonic acid), ethylene-diamine-tetra-(methylenephosphonic acid) (EDTMP) and diethylene-triamine-penta-(methylenephosphonic acid) (DTPMP) and mixtures thereof.

Examples of other chelants suitable for use herein include but are not limited to polyethyleneimines, polyphosphoric acid chelants, etidronic acid, Methylglycine diacetic acid, N-(2-hydroxyethyl)iminodiacetic acid, Iminodisuccinic acid, N,N-Dicarboxymethyl-L-glutamic acid and N-lauroyl-N,N',N"-ethylenediamine diacetic acid.

In some embodiments, the non-diluted and diluted hair colouring compositions of the invention comprise a carboxylic acid chelant, a phosphonic acid chelant, a polyphosphoric acid chelant, salts thereof, or mixtures thereof. In certain embodiments, the compositions of the invention comprise diethylenetriamine pentaacetic acid (DTPA), ethylenediamine-N,N'-disuccinic acid (EDDS), ethylenediamine-N,N'-diglutaric acid (EDDG), 2-hydroxypropylenediamine-N,N'-disuccinic acid (HPDDS), glycinamide-N,N'-disuccinic acid (GADS), ethylenediamine-N—N'-bis(ortho-hydroxyphenyl acetic acid) (EDDHA), diethylene-triamine-penta-(methylenephosphonic acid) (DTPMP), salts thereof, or mixtures thereof. In further embodiments, the compositions of the invention comprise from 0.1% to 5% of diethylene-triamine-penta-(methylenephosphonic acid) and from 0.1% to 5% of ethylenediamine-N,N'-disuccinic acid.

Radical Scavenger

The non-diluted and diluted hair colouring compositions according to the present invention may comprise a radical scavenger. As used herein the term radical scavenger refers to a species that can react with a radical, preferably a carbonate radical to convert the radical species by a series of fast reactions to a less reactive species. The radical scavenger is also preferably selected such that it is not an identical species as the alkalising agent and is present in an amount sufficient to reduce the damage to the hair during the colouring/bleaching process. The non-diluted and/or diluted hair colouring compositions of the present invention may comprise from 0.1% to 10% by weight, preferably from 1% by weight to 7% by weight of a radical scavenger.

Suitable radical scavengers for use herein may be selected from the classes of alkanolamines, amino sugars, amino acids, esters of amino acids and mixtures thereof. Suitable compounds include 3-amino-1-propanol, 4-amino-1-butanol, 5-amino-1-pentanol, 1-amino-2-propanol, 1-amino-2-butanol, 1-amino-2-pentanol, 1-amino-3-pentanol, 1-amino-4-pentanol, 3-amino-2-methylpropan-1-ol, 1-amino-2-methylpropan-2-ol, 3-aminopropane-1,2-diol, glucosamine, N-acetylglucosamine, glycine, arginine, lysine, proline, glutamine, histidine, sarcosine, serine, glutamic acid, tryptophan, or mixtures thereof, or the salts, such as the potassium, sodium, or ammonium salts thereof, or mixtures thereof. The compositions may comprise glycine, sarcosine, lysine, serine, 2 methoxyethylamine, glucosamine, glutamic acid, morpholine, piperidine, ethylamine, 3 amino-1-propanol, or mixtures thereof.

Solvent

The non-diluted and diluted hair colouring compositions of the present invention may comprise a solvent. The solvent may be selected from water or a mixture of water and at least one organic solvent to dissolve the compounds that would not typically be sufficiently soluble in water. Suitable organic solvents for use herein include, but are not limited to: C1 to C4 lower alkanols (e.g., ethanol, propanol, isopropanol), aromatic alcohols (e.g. benzyl alcohol and phenoxyethanol); polyols and polyol ethers (e.g., carbitols, 2-butoxyethanol, propylene glycol, propylene glycol monomethyl ether, diethylene glycol monoethyl ether, monomethyl ether, hexylene glycol, glycerol, ethoxy glycol, butoxydiglycol, ethoxydiglycerol, dipropyleneglycol, polygylcerol), and propylene carbonate. When present, organic solvents are typically present in an amount ranging from 1% to 30%, by weight of the non-diluted and/or diluted hair colouring compositions. The solvent may comprise water, ethanol, propanol, isopropanol, glycerol, 1,2-propylene glycol, hexylene glycol, ethoxy diglycol, or mixtures thereof.

Thickeners

The non-diluted and diluted hair colouring compositions may comprise a thickener in an amount sufficient to provide the composition with a viscosity so that it can be readily applied to the hair without unduly dripping off the hair and causing mess. Typically, such an amount will be at least 0.1%, in some embodiments, at least 0.5%, in other embodiments, at least 1%, by weight of the non-diluted or diluted hair colouring composition. Preferred polymeric thickeners include a polymer thickener, comprising at least one polymer selected from associative polymers, polysaccharides, non-associative polycarboxylic polymers, and mixtures thereof.

As used herein, the expression "associative polymers" means amphiphilic polymers comprising both hydrophilic units and hydrophobic units, for example, at least one C8 to C30 fatty chain and at least one hydrophilic unit. Associative polymers are capable of reversibly combining with each other or with other molecules. Representative associative thickeners that may be used are associative polymers chosen from:
(i) nonionic amphiphilic polymers comprising at least one hydrophilic unit and at least one fatty-chain unit;
(ii) anionic amphiphilic polymers comprising at least one hydrophilic unit and at least one fatty-chain unit;

(iii) cationic amphiphilic polymers comprising at least one hydrophilic unit and at least one fatty-chain unit; and
(iv) amphoteric amphiphilic polymers comprising at least one hydrophilic unit and at least one fatty-chain unit.

The nonionic amphiphilic polymers comprising at least one fatty chain and at least one hydrophilic unit may, for example, be chosen from:
(1) celluloses modified with groups comprising at least one fatty chain; for example: hydroxyethylcelluloses modified with groups comprising at least one fatty chain chosen from alkyl, alkenyl and alkylaryl groups;
(2) hydroxypropyl guars modified with groups comprising at least one fatty chain;
(3) polyether urethanes comprising at least one fatty chain, such as C8-C30 alkyl or alkenyl groups;
(4) copolymers of vinylpyrrolidone and of fatty-chain hydrophobic monomers;
(5) copolymers of C1-C6 alkyl acrylates or methacrylates and of amphiphilic monomers comprising at least one fatty chain;
(6) copolymers of hydrophilic acrylates or methacrylates and of hydrophobic monomers comprising at least one fatty chain.

The anionic amphiphilic polymers comprising at least one hydrophilic unit and at least one fatty-chain unit, may, for example, be chosen from those comprising at least one fatty-chain allyl ether unit and at least one hydrophilic unit comprising an ethylenic unsaturated anionic monomeric unit, for example, a vinylcarboxylic acid unit and further, for example, chosen from units derived from acrylic acids, methacrylic acids and mixtures thereof, wherein the fatty-chain allyl ether unit corresponds to the monomer of formula below:

$$CH_2=C(R1)CH_2OB_nR \quad (I)$$

in which R1 is chosen from H and CH3, B is an ethyleneoxy radical, n is chosen from zero and integers ranging from 1 to 100, R is chosen from hydrocarbon-based radicals chosen from alkyl, alkenyl, arylalkyl, aryl, alkylaryl and cycloalkyl radicals, comprising from 8 to 30 carbon atoms, and, further, for example, from 10 to 24 carbon atoms and even further, for example, from 12 to 18 carbon atoms.

The anionic amphiphilic polymers may further be chosen, for example, from those comprising at least one hydrophilic unit of unsaturated olefinic carboxylic acid type, and at least one hydrophobic unit of the type such as a (C8-C30) alkyl ester or (C8-C30) oxyethylenated alkyl ester of an unsaturated carboxylic acid. The hydrophilic unit of unsaturated olefinic carboxylic acid type corresponds to, for example, the monomer of formula (II) below:

$$CH_2=C(R1)COOH \quad (II)$$

in which R1 is chosen from H, CH3, C2H5 and CH2COOH, i.e. acrylic acid, methacrylic, ethacrylic and itaconic acid units. And the hydrophobic unit of the type such as a (C8-C30) alkyl ester or (C8-C30) oxyethylenated alkyl ester of an unsaturated carboxylic acid corresponds to, for example, the monomer of formula (III) below:

$$CH_2=C(R1)COOB_nR2 \quad (III)$$

in which R1 is chosen from H, CH3, C2H5 and CH2COOH (i.e. acrylate, methacrylate, ethacrylate and itaconate units), B is an ethyleneoxy radical, n is chosen from zero and integers ranging from 1 to 100, R2 is chosen from C8-C30 alkyl radicals, for example, C12-C22 alkyl radical.

Representative anionic amphiphilic polymers that can be used may further be cross-linked. The crosslinking agent can be a monomer comprising a group (IV)

$$CH_2=C< \quad (IV)$$

with at least one other polymerizable group whose unsaturated bonds are not conjugated with respect to one another. Mention may be made, for example, of polyallyl ethers such as polyallylsucrose and polyallyl pentaerythritol.

The cationic amphiphilic polymers used are, for example, chosen from quaternized cellulose derivatives and polyacrylates comprising amino side groups. The quaternized cellulose derivatives are, for example, chosen from quaternized celluloses modified with groups comprising at least one fatty chain, such as alkyl, arylalkyl and alkylaryl groups comprising at least 8 carbon atoms, and mixtures thereof, quaternized hydroxyethylcelluloses modified with groups comprising at least one fatty chain, such as alkyl, arylalkyl and alkylaryl groups comprising at least 8 carbon atoms, and mixtures thereof. The alkyl radicals borne by the above quaternized celluloses and hydroxyethylcelluloses, for example, contain from 8 to 30 carbon atoms. The aryl radicals, for example, are chosen from phenyl, benzyl, naphthyl and anthryl groups.

Among amphoteric amphiphilic polymers comprising at least one hydrophilic unit and at least one fatty-chain unit, mention may be made, for example, of methacrylamidopropyltrimethylammonium chloride/acrylic acid/C8-C30 alkyl methacrylate copolymers, wherein the alkyl radical is, for example, a stearyl radical.

Preferable associative polymeric thickeners for use herein comprise at least one hydrophilic unit which is unsaturated carboxylic acid or its derivative, and at least one hydrophobic unit which is a C8 to C30 alkyl ester or oxyethylenated C8-C30 alkyl ester of unsaturated carboxylic acid. The unsaturated carboxylic acid is preferably acrylic acid, methacrylic acid or itaconic acid. Examples can be made of materials sold under trade name Aculyn-22, Permulen TR1, Carbopol 2020, Carbopol Ultrez-21, Structure 2001, Structure 3001. Another preferable associative polymer for use in the polymer thickening systems of the present invention include polyether polyurethane, for example materials Aculyn-44, Aculyn-46. Another preferable associative polymer for use herein is cellulose modified with groups comprising at least one C8-C30 fatty chain, such as Natrosol Plus Grade 330 CS.

Non-associative cross-linked polycarboxylic polymers for use herein can be chosen, for example, from: (i) cross-linked acrylic acid homopolymers; (ii) copolymers of acrylic or (meth)acrylic acid and of C1-C6 alkyl acrylate or (meth) acrylate. Preferable polymers are Carbopol 980, 981, 954, 2984, 5984, Synthalen M/L/K, Aculyn-33.

The polysaccharides for use herein are, for example, chosen from glucans, modified and unmodified starches (such as those derived, for example, from cereals, for instance wheat, corn or rice, from vegetables, for instance yellow pea, and tubers, for instance potato or cassaya), amylose, amylopectin, glycogen, dextrans, celluloses and derivatives thereof (methylcelluloses, hydroxyalkylcelluloses, ethyl hydroxyethylcelluloses, and carboxymethylcelluloses), mannans, xylans, lignins, arabans, galactans, galacturonans, chitin, chitosans, glucuronoxylans, arabinoxylans, xyloglucans, glucomannans, pectic acids and pectins, alginic acid and alginates, arabinogalactans, carrageenans, agars, glycosaminoglucans, gum arabics, gum tragacanths, ghatti gums, karaya gums, carob gums, galactomannans, such as guar gums, and nonionic derivatives thereof (hydroxypropyl guar) and biopolysaccharides, such as xanthan gums, gellan gums, welan gums, scleroglucans, succinoglycans and mixtures thereof.

For example, suitable polysaccharides are described in "Encyclopedia of Chemical Technology", Kirk-Othmer, Third Edition, 1982, volume 3, pp. 896-900, and volume 15, pp. 439-458, in "Polymers in Nature" by E. A. MacGregor and C. T. Greenwood, published by John Wiley & Sons, Chapter 6, pp. 240-328, 1980, and in "Industrial Gums—Polysaccharides and their Derivatives", edited by Roy L. Whistler, Second Edition, published by Academic Press Inc., the content of these three publications being entirely incorporated by reference.

The polysaccharide is preferably a bio-polysaccharide, particularly preferable are bio-polysaccharides selected from xanthan gum, gellan gum, welan gum, scleroglucan or succinoglycan, for example materials such as Keltrol T, Rheozan. Another preferable polysaccharide is hydroxypropyl starch derivative, particularly preferable hydroxypropyl starch phosphate, for example Structure XL®.

Suitable for use herein are salt tolerant thickeners, including but not limited to: xanthan, guar, hydroxypropyl guar, scleroglucan, methyl cellulose, ethyl cellulose (as AQUA-COTE), hydroxyethyl cellulose (NATROSOL), carboxymethyl cellulose, hydroxypropylmethyl cellulose, microcrystalline cellulose, hydroxybutylmethyl cellulose, hydroxypropyl cellulose (as KLUCEL), hydroxyethyl ethyl cellulose, cetyl hydroxyethyl cellulose (as NATROSOL Plus 330), N-vinylpyrollidone (as POVIDONE), Acrylates/Ceteth-20 Itaconate Copolymer (as STRUCTURE 3001), hydroxypropyl starch phosphate (as STRUCTURE ZEA), polyethoxylated urethanes or polycarbamyl polyglycol ester (e.g. PEG-150/Decyl/SMDI copolymer (as ACULYN 44), PEG-150/Stearyl/SMDI copolymer (as ACULYN 46), trihydroxystearin (available as THIXCIN), acrylates copolymer (e.g. as ACULYN 33) or hydrophobically modified acrylate copolymers (e.g. Acrylates/Steareth-20 Methacrylate Copolymer (as ACULYN 22), acrylates/steareth-20 methacrylate crosspolymer (as ACULYN 88), acrylates/vinyl neodecanoate crosspolymer (available as ACULYN 38), acrylates/beheneth-25 methacrylate copolymer (as ACULYN 28), acrylates/C10-30 alkyl acrylate crosspolymer (as Carbopol® ETD 2020), non-ionic amphophilic polymers comprising at least one fatty chain and at least one hydrophilic unit selected from polyether urethanes comprising at least one fatty chain, and blends of Ceteth—10 phosphate, Di-cetyl phosphate and Cetearyl alcohol (as CRODAFOS CES).

Preferred thickeners for use in the first developer component include acrylates copolymer, hydrophobically modified acrylate copolymers (e.g. Acrylates/Steareth-20 Methacrylate Copolymer) and mixtures thereof. Preferred thickeners polymers for use in the dye component include, blends of Ceteth—10 phosphate, Di-cetyl phosphate and Cetearyl alcohol (as CRODAFOS CES).

Gel Network Thickener System

The non-diluted and diluted hair colouring compositions of the present invention may comprise at least one gel network thickener system. Said system may comprise at least one low HLB surfactant and/or amphophile having a high melting point, and at least one additional second surfactant as specified hereinafter. Suitable gel network thickener systems are disclosed in PCT application WO2006/060568A1.

Said low HLB surfactant and/or amphophile may have preferably an HLB of 6 or less and melting point of at least 30° C. It may be selected from the group consisting of cetyl, stearyl, cetostearyl or behenyl alcohols, steareth-2, glycerol monostearate and mixtures thereof. Said second surfactant may be anionic, non-ionic or cationic. Anionic surfactants may be selected from the group consisting of alkyl ether phosphates having in average 1-3 ethylene oxide units and comprising an alkyl radical comprising from 8 to 30 carbon atoms. Said non-ionic surfactants may be selected from the group consisting of those comprising one or more polyethyleneoxide chain including polyoxyethylene alkyl ethers having from 100 to 200 ethylene oxide units (e.g. steareth-100, steareth-150). Said cationic surfactant may be selected from the group consisting of behentrimonium chloride, behenamidopropyltrimonium methosulfate, stearamidopropyltrimonium chloride, arachidtrimonium chloride and mixtures thereof. A preferred gel network thickening system comprises fatty alcohols having 14 to 30 carbon atoms (cetyl and/or stearyl alcohol) and alkyl ether phosphates (e.g. from 1 to 3 ethylene oxide units). The non-diluted and/or the diluted compositions of the present invention may comprise a total amount of gel network thickening system of from 2% to 10% by weight of the non-diluted or diluted hair colouring composition. The weight ratio of the low HLB surfactants to the second specified surfactants is preferably from 10:1 to 1:1.

Carbonate Ion Source

The non-diluted and diluted hair colouring compositions of the present invention may comprise a source of carbonate ions, carbamate ions, or hydrogen carbonate ions, in a sufficient amount to reduce damage to the hair during the colouring process. Such an amount may range from 0.1% to 15%, or from 0.1% to 10%, or from 1% to 7%, by weight of the non-diluted or diluted hair colouring composition. Suitable sources for the ions include but are not limited to: sodium carbonate, sodium hydrogen carbonate, potassium carbonate, potassium hydrogen carbonate, guanidine carbonate, guanidine hydrogen carbonate, lithium carbonate, calcium carbonate, magnesium carbonate, barium carbonate, ammonium carbonate, ammonium hydrogen carbonate and mixtures thereof. In some embodiments, the source of carbonate ions is sodium hydrogen carbonate, potassium hydrogen carbonate, or mixtures thereof. The source of carbonate ions may be ammonium carbonate, ammonium hydrogen carbonate, or mixtures thereof.

Conditioning Agent

The non-diluted and diluted hair colouring compositions may comprise a conditioning agent. The conditioning agent may be present in the developer component, the dye component, the dilutant component, a separate conditioner component or any combination thereof. Conditioning agents suitable for use herein are selected from silicone materials, amino silicones, C6 to C30 fatty alcohols, polymeric resins, polyol carboxylic acid esters, cationic polymers, cationic surfactants, insoluble oils and oil derived materials and mixtures thereof. Additional materials include mineral oils and other oils such as glycerin and sorbitol. Particularly useful conditioning materials are cationic polymers. Conditioners of cationic polymer type can be chosen from those comprising units of at least one amine group chosen from primary, secondary, tertiary and quaternary amine groups that may either form part of the main polymer chain, or be borne by a side substituent that is directly attached to the main polymer chain, described hereinafter. The conditioning agent will generally be used at levels of from 0.05% to 20%, preferably of from 0.1% to 15%, more preferably of from 0.2% to 10%, even more preferably of from 0.2% to 2% by weight of the non-diluted or diluted hair colouring composition. The conditioning agent may be included in a separate pre- or post-treatment composition.

Silicones can be selected from polyalkylsiloxane oils, linear polydimethylsiloxane oils containing trimethylsilyl or hydroxydimethylsiloxane endgroups, polymethylphenylsiloxane, polydimethylphenylsiloxane or polydimethyldiphenylsiloxane oils, silicone resins, organofunctional siloxanes having in their general structure one or a number of organofunctional group(s), the same or different, attached directly to the siloxane chain or mixtures thereof. Said organofunctional group(s) are selected from: polyethyleneoxy and/or polypropyleneoxy groups, (per)fluorinated groups, thiol groups, substituted or unsubstituted amino groups, carboxylate groups, hydroxylated groups, alkoxylated groups, quaternium ammonium groups, amphoteric and betaine groups. The silicone can either be used as a neat fluid or in the form of a pre-formed emulsion.

Suitable silicones include silicones containing groups that may be ionized into cationic groups, for example aminosilicones containing at least 10 repeating siloxane $(Si(CH_3)_2—O)$ units within the polymer chain, with either terminal, graft, or a mixture of terminal and graft aminofunctional groups. Example functional groups are not limited to aminoethylaminopropyl, aminoethylaminoisobutly, aminopropyl. In the case of graft polymers, the terminal siloxane units can be $(CH_3)_3Si—O$, $R_{12}(CH_3)_2Si—O$, where $R_{12}$ can be either OH or $OR_{13}$, where $R_{13}$ is a C1-C8 alkyl group, or a mixture of both terminal groups. These silicones are also available as preformed emulsions. Commercially available aminosilicones include DC-2-8566, DC 7224, DC-2-8220, SF1708, SM2125, Wacker Belsil ADM 653/1100/1600/652/6057E/8020, DC929, DC939, DC949, SM2059 Aminosilicones may also contain additional functional groups. Additional functional groups can include polyoxyalkylene, the reaction product of amines and carbinols, and alky chains. For example products know as methoxy PEG/PPG-7/3 Aminopropyl Dimethicone, such as Abil Soft AF100, or products know as Bis (C13-15 Alkoxy) PG Amodimethicone, such as DC 8500. Cationic polymers suitable for use herein can be chosen from those comprising units of at least one amine group chosen from primary, secondary, tertiary and quaternary amine groups that may either form part of the main polymer chain or be borne by a side substituent that is directly attached to the main polymer chain. Such cationic polymers generally have a number average molecular mass ranging from 500 to about $5 \times 10^6$, or more preferably from 1000 to $3 \times 10^6$. Preferably the cationic polymers are selected from polymers of the polyamine, polyamino amide and polyquaternary ammonium type.

Polymers of the polyamine, polyamino amide and polyquaternary ammonium type that may be used include but are not limited to:

1) Homopolymers and copolymers derived from acrylic or methacrylic esters or amides. Copolymers of these polymers can also comprise at least one unit derived from comonomers which may be chosen from the family of acrylamides, methacrylamides, diacetone acylamides, acrylamides and methacrylicamides substituted on the nitrogen with at least one group chosen from lower (C1-C4) alkyls, acrylic and methacrylic acids and esters thereof, vinyllactams such as vinylpyrrolidone and vinylcaprolactam, and vinyl esters. Copolymers of acrylamide and of methacryloyloxyethyltrimethylammonium methosulfate, examples of which include polymers known as Polyquaternium-5 (herein referred as PQ"), such as Reten 210/220/230/240/1104/1105/1006, Merquat 5/5SF.

Copolymers of vinylpyrrolidone and dimethylaminopropyl methacrylamide, examples of which include polymers known as PQ-28, such as Gafquat HS-100. Copolymers of vinyl pyrrolidone and dialkyaminoalkyl acrylates or methacrylates, examples of which include polymers known as PQ-11, such as Gafquat 440/734/755/755N, Luviquat PQ11 PM, Polyquat-11 SL. Copolymers vinylpyrrolidone, dimethylaminopropyl methacrylamide and methacryloylaminopropyl lauryldimonium chloride, examples of which include polymers known as PQ-55, such as Styleze W-20. Copolymers of acrylic acid, acrylamide and methacrylamidopropyltrimonium chloride, examples of which include polymers known as PQ-53, such as Merquat 2003. Copolymers of dimethyaminopropylacrylate (DMAPA), acrylic acid and acrylonitrogens and diethyl sulfate, examples of which include polymers known as PQ-31, such as Hypan QT100. Copolymers of acrylamide, acrylamidopropyltrimonium chloride, 2-amidopropylacrylamide sulfonate, and dimethyaminopropylacrylate (DMAPA), examples of which include polymers known as PG-43, such as Bozequat 4000. Copolymers of acrylic acid, methylacrylate and methacrylamidopropyltrimonium chloride, examples of which include polymers known as PQ-47, such as Merquat 2001/2001N. Copolymers of methacryloyl ethyl betaine, 2-hydroxyethyl methacrylate and methacryloyl ethyl trimethyl ammonium chloride, examples of which include polymers known as PQ-48, such as Plascize L-450. Copolymers of acrylic acid diallyl dimethyl ammonium chloride and acrylamide, examples of which include polymers known as PQ-39, such as Merquat 3330/3331. Further examples include copolymers of methacrylamide methacrylamido-propyltrimonium and methacryloylethyltrimethyl ammonium chloride and their derivatives, either homo or copolymerised with other monomers, examples of which include polymers known as: PQ-8, PQ-9, PQ-12, PQ-13; PQ-14, PQ-15, such as Rohagit KF720 F, PQ-30, such as Mexomere PX, PQ-33, PQ-35, PQ-36, such as Plex 3074 L, PQ-45, such as Plex 3073L, PQ-49, such as Plascize L-440, PQ50 such as Plascize L-441, PQ-52.

2) Cationic polysaccharides, such as cationic celluloses and cationic galactomannan gums. Among the cationic polysaccharides that maybe mentioned, for example, are cellulose ether derivatives comprising quaternary ammonium groups and cationic cellulose copolymers or cellulose derivatives grafted with a water-soluble quaternary ammonium monomer and cationic galactomannan gums. Examples include but are not limited to: Copolymers of hydroxyethylcelluloses and diallyldimethyl ammonium chlorides, examples of which include polymers known as PQ-4, such as Celquat L200/H100. Copolymers of hydroxyethylcelluloses and a trimethyl ammonium substituted epoxide, examples of which include polymers known PQ-10, such as AEC Polyquaternium-10, Catinal C-100/HC-35/HC-100/HC-200/LC-100/LC-200, Celquat SC-240C/SC-230M, Dekaquat 400/3000, Leogard GP, RITA Polyquta 400/3000, UCARE Polymer JR-125/JR-400/JR-30M/LK/LR400/LR30M. Copolymers of hydroxyethylcelluloses and lauryl dimethyl ammonium substituted epoxides, examples of which include polymers known as PQ-24, such as Quatrisoft polymer LM-200. Derivatives of Hydroxypropyl Guar, examples of which include polymers known as Guar Hydroxypropyltrimonium Chloride, such as Catinal CG-100/CG-200, Cosmedia Guar C-261N/C-261N/C-261N, DiaGum P 5070, N-Hance Cationic Guar, Hi-Care 1000, Jaguar C-17/C-2000/C-13S/C-14S/Excel, Kiprogum CW, Kiprogum NGK. Hydroxypropyl derivatives of Guar Hydroxypropyltrimonium Chloride, examples of which include polymers known as Hydroxypropyl Guar Hydroxypropyltrimonium Chloride, such as Jaguar C-162.

3) Polyamino amide derivatives resulting from the condensation of polyalkylene polyamines with polycarboxylic acids followed by alkylation with difunctional agents. Among the derivative, mention may be made for example to adipic acid/dimethylaminohydroxypropyl/diethylenetriamine.

4) Polymers obtained by reaction of a polyalkylene polyamine comprising two primary amines groups and at last one secondary amine group with a decarboxylic acid chosen from diglycolic acids and saturated aliphatic dicarboxylic acids comprising from 3 to 8 carbon atoms. Non-limiting examples of such derivatives include the adipic acid/epxoypropyl/diethylenetriamine.

5) Cyclopolymers of dialkdiallylamine or of dialkyldiallyammonium, among which polymers mention may be made of: Dimethyldiallyammonium chloride polymers, examples of which include polymers known as PQ-6, such as Merquat 100, Mirapol 100, Rheocare CC6, AEC polyquaternium-6, Agequat 400, Conditioner P6, Flocare C106, Genamin PDAC, Mackernium 006. Copolymers of acrylamides and dimethyldiallylammonium chlorides monomers, examples of which include polymers known as PQ-7, such as AEC Polyquaternium-7, Agequat-5008/C-505, Conditioner P7, Flocare C107, Mackernium 007/007S, ME Polymer 09W, Merquat 550/2200/S, Mirapol 550, Rheocare CC7/CCP7, Salcare HSP-7/SC10/Super 7. Copolymers of dimethyldiallylammoniumchlorides and acrylic acids, examples of which include polymers known as polyquaternary-22, such as Merquat 280/Merquat 295.

6) Quaternary diammonium polymers comprising repeat units corresponding to [−N+(R1)(R2)-A1-N+(R3)(R4)-B1-][2X-], in which R1, R2, R3 and R4, which may be identical or different, are chosen from aliphatic, alicyclic and arylaliphatic radicals comprising from 1 to 20 carbon atoms and from lower hydroxyalkylaliphatic radicals, or R1, R2, R3 and R4, together or separately, constitute, with the nitrogen atoms to which they are attached, heterocycles optionally comprising a second heteroatom other then nitrogen, or R1, R2, R3 and R4, are chosen from liner or branched C1-C6 alkyl radicals substituted with at least one group chosen from nitrile, ester, acyl and amide groups and groups of —CO—O—R5-D and —CO—NH—R5-D wherein R5 is chosen from alkylene groups and D is chosen from quaternary ammonium groups. A1 and B1, which may be identical or different, are chosen from linear and branched, saturated or unsaturated polymethylene groups comprising 2 to 20 carbon atoms. The polymethylene groups may comprise, linked to or intercalated in the main ring, at least one entity chosen from aromatic rings, oxygen and sulphur atoms and sulphoxide, sulphone, disulphide, amino, alkylamino, hydroxyl, quaternary, ammonium, ureido, amide and ester groups, and X— is an anion derived from inorganic and organic acids. D is chosen from a glycol residue, a bis-secondary diamine residue, a bis-primary diamine residue or a ureylene group. An examples of which include polymers known as Hexadimethrine chloride, where R1, R2, R3 and R4 are each methyl radicals, A1 is (CH2)3 and B1 is (CH2)6 and X=Cl. Further examples of which include polymers known as PQ-34 where R1 and R2 are ethyl radicals and R3 and R4 are methyl radicals and A1 is (CH2)3 and B1 is (CH2)3 and X=Br, such as Mexomere PAX.

7) Polyquaternary ammonium polymers comprising repeating units of formula [−N+(R6)(R7)-(CH2)r-NH—CO—(CH2)q-(CO)t-NH—(CH2)s-N+(R8)(R9)-A-][2X-], in which R6, R7, R8 and R9 which may be identical or different, are chosen from a hydrogen atom and a methyl, ethyl, propyl, hydroxyethyl, hydroxypropyl, and —CH2CH2(OCH2CH2) pOH radicals, wherein p is equal to 0 or an integer ranging from 1 to 6, wherein R6, R7, R8 and R9 do not all simultaneously represent a hydrogen atom. R and s which maybe identical or different are each an integer ranging from 1 to 6, q is equal to 0 or an integer ranging from 1 to 34 and X— is anion such as a halide. T is an integer chosen to be equal to 0 or 1. A is chosen from divalent radicals such as —CH2-CH2-O—CH2-CH2-. Examples of which include: Polymers known as PQ-2, where r=s=3, q=0, t=0, R6, R7, R8 and R9 are methyl groups, and A is —CH2-CH2-O—CH2-CH2, such as Ethpol PQ-2, Mirapol A-15. Polymers known as PQ-17 where r=s=3, q=4, t=1 R6, R7, R8 and R9 are methyl groups, and A is —CH2-CH2-O—CH2-CH2. Polymers known as PQ-18, where r=s=3, q=7, t=1 R6, R7, R8 and R9 are methyl groups, and A is —CH2-CH2-O—CH2-CH2. Polymers known as the block copolymer formed by the reaction of Polyquaternium-2 with Polyquaternium-17, known as PQ-27, such as Mirapol 175.

8) Copolymers of vinylpyrrolidones and of vinylimidazoles and optionally vinylcaprolactums, examples of which include polymers known as PQ-16 formed from methylvinylimidazolium chlorides and vinylpyrrolidones, such as Luviquat FC370/FC550/FC905/HM-552. Or copolymers of vinylcaprolactams and vinylpyrrolidones with methylvinylimidazolium methosulfates, examples of which include polymers known as PQ-46, such as Luviquat Hold. Or copolymers of vinylpyrrolidones and quaternized imidazolines, examples of which include polymers known PQ-44, such as Luviquat Care.

9) Polyamines such as the product Polyquart H sold by Cognis under the reference name polyethylene glycol (15) tallow polyamine in the CTFA dictionary.

10) Cross linked methacryloyloxy(C1-C4)alkyltri(C1-C4) alkylammonium salt polymers such as the polymers obtained by homopolymerisation of dimethylaminoethyl methacrylates quaternized with methyl chloride, or by copolymerisation of acrylamides with dimethylaminoethyl methacrylates quaternized with methyl chloride, the homo or copolymerisation being followed by crosslinking with a compound comprising olefinic unsaturation, such as methylenebisacrylamides, examples of which include polymers known as PQ-37, such as Synthalen CN/CR/CU, or as a dispersion in another media such as Salcare SC95/SC96, Rheocare CTH(E). Or in another example of which include polymers known as PQ-32, or when sold as a dispersion in mineral oil such as Salcare SC92.

11) Further examples of cationic polymers include polymers known as PQ-51, such as Lipidure-PMB, as PQ-54, such as Qualty-Hy, as PQ-56 such as Hairrol UC-4, and as PQ-87 such as Luviquat sensation.

12) Silicone polymers comprising cationic groups and/or groups which may be ionised into cationic groups. For example: cationic silicones of the general formula (R10-N+(CH3)2)-R11-(Si(CH3)2-O)x-R11-(N+(CH3)2)-R10), where R10 is an alkyl derived from coconut oil, and R11 is (CH2CHOCH2-O—(CH2)3 and x is a number between 20 and 2000, examples of which include polymers known as Quaternium 80, such as Abil Quat 3272/3474.

Silicones containing groups which may be ionised into cationic groups, for example aminosilicones containing at least 10 repeating siloxane —(Si(CH3)2-O) units within the polymer chain, with either terminal, graft or a mixture of terminal and graft aminofunctional groups. Example functional groups are not limited to aminoethylaminopropyl, aminoethylaminoisobutly, aminopropyl. In the case of graft polymers, the terminal siloxane units can either be (CH3)3Si—O or R12(CH3)2Si—O, where R12 can be either OH or OR13, where R13 is a C1-C8 alky group, or a mixture of both functional terminal groups. These silicones are also available as preformed emulsions. Polymer with terminal siloxane units of (CH3)3Si—O examples of which include polymers known as trimethylsilylamodimethicone, such as DC-2-8566, DC 7224, DC-2-8220, SF1708, SM 2125, Wacker Belsil ADM 653. Further examples include polymers with terminal siloxane units of (R120)(CH3)2Si—O where R12 can be either OH or OR13, where R13 is a C1-C8 alky group, or a mixture of both functional terminal groups, known as amodimethicone, such as Wacker Belsil ADM 1100/ADM 1600/ADM 652/ADM 6057E/ADM 8020, DC929, DC939, DC949, SM2059. Silicones containing groups which may be ionised into cationic groups—for example silicones containing at least 10 repeating siloxane —(Si(CH3)2-O) units within the polymer chain, with either terminal, graft or a mixture of terminal and graft aminofunctional groups, together with additional functional groups. Additional functional groups can include polyoxyalkylene, the reaction product of amines and carbinols, alky chains. For example products know as methoxy PEG/PPG-7/3 Aminopropyl Dimethicone, such as Abil Soft AF100. For example products know Bis (C13-15 Alkoxy) PG Amodimethicone, such as DC 8500.

The non-diluted and diluted hair colouring compositions and/or components of the present invention may comprise at least 0.2%, or from 0.5% to 2% by weight of the composition of a cationic polymer.

Surfactants

The non-diluted and diluted hair colouring compositions according to the present invention may comprise one or more surfactants. Surfactants suitable for use herein generally have a lipophilic chain length of from 8 to 30 carbon atoms and can be selected from anionic, nonionic, amphoteric and cationic surfactants and mixtures thereof. The total level of surfactant may be from 2% to 30%, or from 8% to 25%, or from 10% to 20% by weight of the non-diluted or diluted hair colouring composition.

The developer component may comprise from 0 to 5% by weight of surfactant. The dye component may comprise from 0 to 10% by weight of surfactant.

The dilutant component may comprise less than 10%, preferably less than 8%, more preferably less than 6% by weight of surfactant, even more preferably is substantially free of surfactant. The inventors have surprisingly found that if a dilutant component comprising a too high level of surfactant is added to the second portion of the non-diluted hair colouring composition to obtain the diluted hair colouring composition, a substantial drop of viscosity may be observed to such an extent that the viscosity of the diluted hair colouring composition may be too low to be applied to the hair lengths and tips and without dripping from the hair.

Anionic surfactants, where may be present in the range of from 0.1% to 20%, or from 0.1% to 15%, or from 5% to 15% by weight of the non-diluted or diluted hair colouring composition; amphoteric or nonionic surfactants, may independently be present is in the range of from 0.1% to 15%, or from 0.5% to 10%, or from 1% to 8% by weight of the non-diluted or diluted hair colouring composition.

Suitable anionic surfactants, which can be used, alone or as mixtures, include salts (such as alkaline salts, for example, sodium salts, ammonium salts, amine salts, amino alcohol salts and magnesium salts) of the following compounds: alkyl sulphates, alkyl ether sulphates, alkylamido ether sulphates, alkylarylpolyether sulphates, monoglyceride sulphates; alkyl sulphonates, alkyl phosphates, alkylamide sulphonates, alkylaryl sulphonates, a-olefin sulphonates, paraffin sulphonates; alkyl sulphosuccinates, alkyl ether sulphosuccinates, alkylamide sulphosuccinates; alkyl sulphosuccinamates; alkyl sulphoacetates; alkyl ether phosphates; acyl sarcosinates; acyl isethionates and N-acyltaurates. The alkyl or acyl radical of all of these various compounds, for example, comprises from 8 to 24 carbon atoms, and the aryl radical, for example, is chosen from phenyl and benzyl groups. Among the anionic surfactants, which can also be used, mention may also be made of fatty acid salts such as the salts of oleic, ricinoleic, palmitic and stearic acids, coconut oil acid or hydrogenated coconut oil acid; acyl lactylates in which the acyl radical comprises from 8 to 20 carbon atoms. Weakly anionic surfactants can also be used, such as alkyl-D-galactosiduronic acids and their salts, as well as polyoxyalkylenated ($C_6$-$C_{24}$) alkyl ether carboxylic acids, polyoxyalkylenated ($C_6$-$C_{24}$) alkylaryl ether carboxylic acids, polyoxyalkylenated ($C_6$-$C_{24}$) alkylamido ether carboxylic acids and their salts, for example, those comprising from 2 to 50 ethylene oxide groups, and mixtures thereof. Anionic derivatives of polysaccharides, for example carboxyalkyl ether of alkyl polyglucosides, can be also used.

The nonionic surfactants are compounds that are well known (see, for example, in this respect "Handbook of Surfactants" by M. R. Porter, published by Blackie & Son (Glasgow and London), 1991, pp. 116-178). They can be chosen, for example, from polyethoxylated, polypropoxylated and polyglycerolated fatty acids, alkyl phenols, α-diols and alcohols comprising a fatty chain comprising, for example, from 8 to 18 carbon atoms, it being possible for the number of ethylene oxide or propylene oxide groups to range, for example, from 2 to 200 and for the number of glycerol groups to range, for example, from 2 to 30. Mention may also be made of copolymers of ethylene oxide and of propylene oxide, condensates of ethylene oxide and of propylene oxide with fatty alcohols; polyethoxylated fatty amides preferably having from 2 to 30 mol of ethylene oxide and their monoethanolamine and diethanolamine derivatives, polyglycerolated fatty amides, for example, comprising on average from 1 to 5, and such as from 1.5 to 4, glycerol groups; polyethoxylated fatty amines such as those containing from 2 to 30 mol of ethylene oxide; oxyethylenated fatty acid esters of sorbitan having from 2 to 30 mol of ethylene oxide; fatty acid esters of sucrose, fatty acid esters of polyethylene glycol, alkylpolyglycosides, N-alkylglucamine derivatives, amine oxides such as ($C_{10}$-$C_{14}$)alkylamine oxides or N-acylaminopropylmorpholine oxides.

The amphoteric surfactants can be chosen, for example, from aliphatic secondary and tertiary amine derivatives in which the aliphatic radical is chosen from linear and branched chains comprising from 8 to 22 carbon atoms and comprising at least one water-soluble anionic group (for example carboxylate, sulphonate, sulphate, phosphate or phosphonate); mention may also be made of ($C_8$-$C_{20}$)alkylbetaines, sulphobetaines, ($C_8$-$C_{20}$)alkylamido($C_1$-$C_6$)alkylbetaines or ($C_8$-$C_{20}$)alkylamido($C_1$-$C_6$)alkylsulphobetaines. Among the amine derivatives, mention may be made of the products sold under the name Miranol, as described, for example, in U.S. Pat. Nos. 2,528,378 and 2,781,354 and having the structures of: $R_2$—CON HCH$_2$CH$_2$—N$^+$($R_3$)($R_4$)(CH$_2$COO$^-$), (VI) in which: $R_2$ is chosen from alkyl radicals derived from an acid $R_2$—COOH present in hydrolysed coconut oil, and heptyl, nonyl and undecyl radicals, $R_3$ is a β-hydroxyethyl group and $R_4$ is a carboxymethyl group; and of $R_5$—CONHCH$_2$CH$_2$—N(B)(C) (VII) wherein B represents —CH$_2$CH$_2$OX', C represents —(CH$_2$)$_z$—Y', with z=1 or 2, X' is chosen from the —CH$_2$CH$_2$—COOH group and a hydrogen atom, Y' is chosen from —COOH and —CH$_2$—CHOH—SO$_3$H radicals, $R_5$ is chosen from alkyl radicals of an acid $R_5$—COOH present in coconut oil or in hydrolysed linseed oil, alkyl radicals, such as $C_7$, $C_9$, $C_{11}$ and $C_{13}$ alkyl radicals, a $C_{17}$ alkyl radical and its iso form, and unsaturated $C_{17}$ radical. These compounds are classified in the CTFA dictionary, 5th edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium capryloamphodipropionate, lauroamphodipropionic acid, and cocoamphodipropionic acid. Salts of diethyl aminopropyl cocoaspartamid can be also used.

The cationic surfactants may be chosen from: A) the quaternary ammonium salts of general formula (VIII) below:

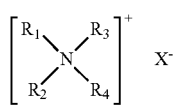

(VIII)

wherein X⁻ is an anion chosen from halides (chloride, bromide and iodide), $(C_2-C_6)$alkyl sulphates, such as methyl sulphate, phosphates, alkyl and alkylaryl sulphonates, and anions derived from organic acids, such as acetate and lactate, and i) the radicals $R_1$ to $R_3$, which may be identical or different, are chosen from linear and branched aliphatic radicals comprising from 1 to 4 carbon atoms, and aromatic radicals such as aryl and alkylaryl. The aliphatic radicals can comprise at least one hetero atom such as oxygen, nitrogen, sulphur and halogens. The aliphatic radicals are chosen, for example, from alkyl, alkoxy and alkylamide radicals, $R_4$ is chosen from linear and branched alkyl radicals comprising from 16 to 30-carbon atoms. The cationic surfactant is, for example, a behenyltrimethylammonium salt (for example chloride).

ii) the radicals $R_1$ and $R_2$, which may be identical or different, are chosen from linear and branched aliphatic radicals comprising from 1 to 4 carbon atoms, and aromatic radicals such as aryl and alkylaryl. The aliphatic radicals can comprise at least one hetero atom such as oxygen, nitrogen, sulphur and halogens. The aliphatic radicals are chosen, for example, from alkyl, alkoxy, alkylamide and hydroxyalkyl radicals comprising from 1 to 4 carbon atoms; $R_3$ and $R_4$, which may be identical or different, are chosen from linear and branched alkyl radicals comprising from 12 to 30 carbon atoms, the said alkyl radicals comprise at least one function chosen from ester and amide functions. $R_3$ and $R_4$ are chosen, for example, from $(C_{12}-C_{22})$alkylamido$(C_2-C_6)$alkyl and $(C_{12}-C_{22})$ alkylacetate radicals. The cationic surfactant is, for example, a dicetyldimethyl ammonium salt (for example chloride);

B)—the quaternary ammonium salts of imidazolinium, such as that of formula (IX) below:

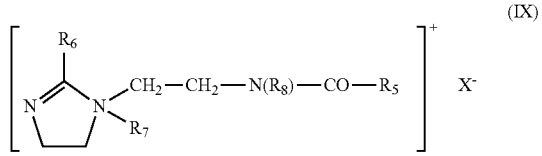

in which $R_5$ is chosen from alkenyl and alkyl radicals comprising from 8 to 30 carbon atoms, for example fatty acid derivatives of tallow, $R_6$ is chosen from a hydrogen atom, $C_1$-$C_4$ alkyl radicals and alkenyl and alkyl radicals comprising from 8 to 30 carbon atoms, $R_7$ is chosen from $C_1$-$C_4$ alkyl radicals, $R_8$ is chosen from a hydrogen atom and $C_1$-$C_4$ alkyl radicals, and X⁻ is an anion chosen from halides, phosphates, acetates, lactates, alkyl sulphates, alkyl sulphonates and alkylaryl sulphonates. $R_5$ and $R_6$ may be, for example, a mixture of radicals chosen from alkenyl and alkyl radicals comprising from 12 to 21 carbon atoms, such as fatty acid derivatives of tallow, $R_7$ is methyl and $R_8$ is hydrogen. Such a product is, for example, Quaternium-27 (CTFA 1997) or Quaternium-83 (CTFA 1997), which are sold under the names "Rewoquat®" W75, W90, W75PG and W75HPG by the company Witco, C)—the diquaternary ammonium salts of formula (X):

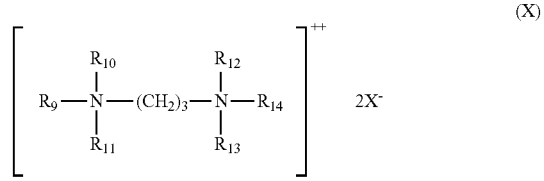

in which $R_9$ is chosen from aliphatic radicals comprising from 16 to 30 carbon atoms, $R_{10}$, $R_{11}$, $R_{12}$, $R_{13}$ and $R_{14}$, which may be identical or different, are chosen from hydrogen and alkyl radicals comprising from 1 to 4 carbon atoms, and X⁻ is an anion chosen from halides, acetates, phosphates, nitrates and methyl sulphates. Such diquaternary ammonium salts, for example, include propanetallowdiammonium dichloride; and D)—the quaternary ammonium salts comprising at least one ester function, of formula (XI) below:

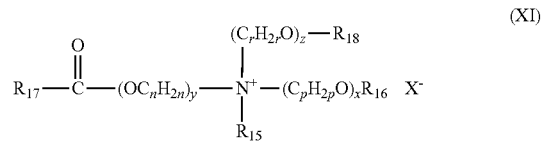

in which: R15 is chosen from C1-C6 alkyl radicals and C1-C6 hydroxyalkyl and dihydroxyalkyl radicals; R16 is chosen from: a radical R19C(O)—, linear and branched, saturated and unsaturated C1-C22 hydrocarbon-based radicals R20, and a hydrogen atom, R18 is chosen from: a radical R21C(O)—, linear and branched, saturated and unsaturated C1-C6 hydrocarbon-based radicals R22, and a hydrogen atom, R17, R19 and R21, which may be identical or different, are chosen from linear and branched, saturated and unsaturated C7-C21 hydrocarbon-based radicals; n, p and r, which may be identical or different, are chosen from integers ranging from 2 to 6; y is chosen from integers ranging from 1 to 10; x and z, which may be identical or different, are chosen from integers ranging from 0 to 10; X— is an anion chosen from simple and complex, organic and inorganic anions; with the proviso that the sum x+y+z is from 1 to 15, that when x is 0, then R16 is R20 and that when z is 0, then R18 is R22.

The ammonium salts of formula (XI) can be used, in which: R15 is chosen from methyl and ethyl radicals, x and y are equal to 1; z is equal to 0 or 1; n, p and r are equal to 2; R16 is chosen from: a radical R19C(O)—, methyl, ethyl and $C_{14}$-$C_{22}$ hydrocarbon-based radicals, and a hydrogen atom; R17, R19 and R21, which may be identical or different, are chosen from linear and branched, saturated and unsaturated C7-C21, hydrocarbon-based radicals; R18 is chosen from: a radical R21C(O)— and a hydrogen atom. Such compounds are sold, for example, under the names Dehyquart by the company Cognis, Stepanquat by the company Stepan, Noxamium by the company Ceca, and Rewoquat WE 18 by the company Rewo-Witco.

Viscosity

The developer component and the dye component may be, independently from one another, prepared as so called thin liquids or creams.

Each of the non-diluted hair colouring composition and the diluted hair colouring composition may have a viscosity which induces a shear stress of from 20 to 200 Pa at 10 s$^{-1}$ as measured according to the viscosity test method.

The non-diluted hair colouring composition may have a viscosity which induces a shear stress of from 60 to 200 Pa at 10 s$^{-1}$ as measured according to the viscosity test method and the diluted hair colouring composition may have a viscosity which induces a shear stress of from 20 to 180 Pa at 10 s$^{-1}$ as measured according to the viscosity test method.

Each of the non-diluted and diluted hair colouring compositions may have a viscosity which induces a shear stress of from 20 to 60 Pa at 10 s$^{-1}$, when the non-diluted and diluted hair colouring compositions are applied to the hair with a container to which a nozzle or a separate applicator device such as a comb or a brush is attached.

The non-diluted hair colouring composition may have a viscosity which induces a shear stress of from 30 to 200 Pa at 10 s$^{-1}$, more preferably from 100 to 200 Pa at 10 s$^{-1}$, even more preferably from 130 to 180 Pa at 10 s$^{-1}$ when the non-diluted hair colouring composition is applied to the hair with a brush and bowl applicator. The diluted hair colouring composition may have a viscosity which induces a shear stress of from 20 to 180 Pa at 10 s$^{-1}$, more preferably from 40 to 180 Pa at 10 s$^{-1}$, even more preferably from 70 to 170 Pa at 10 s$^{-1}$, when the non-diluted hair colouring composition is applied to the hair with a brush and bowl applicator or with the hands or fingers of the user.

Whilst not being bound by theory, it is believed that the provision of the non-diluted compositions having viscosity values as described hereinabove enables the first portion of the non-diluted hair colouring composition to be applied directly to the roots without any dripping or running down the hair lengths and also enables the diluted hair colouring composition to be easily applied and distributed along the entire remaining hair length with minimal to no dripping from the hair.

Another alternative embodiment of the present invention relates to an alternative method for colouring hair Whilst not being bound by theory, it is believed that the overall effective lightening and colouring capacity of the composition that is to be applied to the hair lengths and tips below the roots, versus the composition applied to the hair roots can also be reduced by instructing the consumer to apply a first portion of the non-diluted hair colouring composition to the roots and then wait for a given period of time before applying the second portion of the non-diluted hair colouring composition to the remaining pre-coloured hair length. It is believed that this hair requires less lightening and dye deposition from the applied composition in order to deliver a colour result similar to that resulting from the application of the more concentrated first portion applied to the roots. Whilst not being bound by theory, it is believed that instructing the consumer to wait results in a reduction in the concentration of actives species such as dye precursors, peroxide and alkalizing agent, if present before the dye formation process has completed, thereby still enabling penetration into the hair shaft to provide permanent albeit less hair colour. Such a method may comprise the steps of i) mixing the developer component and the dye component and applying a first portion, preferably up to about 85%, more preferably from 80% to 20%, even more preferably from 75% to 55% and most preferably from 75% to 60% of the mixed composition to the roots/root line of keratinous fibres;
ii) retaining and not applying up to 15% of said mixed composition to the roots;
iii) waiting for a time period of from 10 min to 40 min, preferably from 15 min to 30 min and more preferably from 20 min;
iv) applying the retained second portion of mixed composition to the remaining hair length below about the root line application and waiting for a time period of from about 5 min to 20 min, preferably about 10 min and
v) rinsing the hair;

Application Means

Both the non-diluted hair colouring composition and the diluted hair colouring composition may be applied to the hair with a brush and bowl applicator. Alternatively, the non-diluted hair colouring composition may be applied to the hair with a brush and bowl applicator whereas the diluted hair colouring composition may be applied to the hair with the hands and fingers of the user.

Alternatively, both the non-diluted hair colouring composition and the diluted hair colouring composition may be applied to the hair with a container to which a nozzle or a separate applicator device such as a comb is attached.

The application means may also include means which assist in achieving particular effects such as highlighting such as highlighting combs, brushes and tools, foils and highlighting caps. Additional application means technology can be used to assist in the penetration of the product into the hair. Examples of such technology include heating devices, ultraviolet light devices and ultrasound devices.

Hair Colouring Kit

The present invention also relates to a hair colouring kit which may be used for carrying out the method for colouring hair described hereinbefore.

The kit may comprise a developer component comprising an oxidizing agent, a dye component comprising at least one oxidative dye precursor and/or an alkalising agent and a dilutant component comprising water and optionally at least one active component.

The developer component may comprise from 1 to 20% by weight of the oxidizing agent and the dye component may comprise from 0.01% to 10% by weight of the oxidative dye precursor(s) and/or from 0.1% to 10% by weight of the alkalising agent, and the dilutant component may comprise up to 99% by weight of water and up to 25% by weight of at least one active component selected from surfactants, conditioning agents, polymers, and mixtures thereof.

The kit may further comprise a shampoo for use in rinsing the hair after colouring and/or a conditioner component.

The kits may also comprise a color refresher component. Such colour refresher component may comprise at least one pre-formed dye and may be applied to the hair immediately after the oxidative colour. This is typically during the next wash cycle(s) from 1 day to 60 days after the original oxidative application. This colour refresher component can be used to increase the initial colour obtained and/or boost the colour during the wash and style cycle until the next oxidative colouring or bleaching event.

The present invention may be utilized in a variety of packaging and dispensing devices. These dispensing devices can come in the form of separate devices which may be used independently or in combination with one another. Typically, the hair colouring or bleaching components are contained within separate single or multi compartment containers so that the components can be stored separately from one another before use. The components are then mixed together by a mixing means and then applied to the consumer's hair by an application means.

The developer component, the dye component and the dilutant component may be provided as separate containers in the kit. The developer component container, the dye component container and the dilutant component container may be a bottle, a tube, an aerosol, or a sachet.

The developer component may be provided as a container such as a bottle, a tube, an aerosol, or a sachet and the dye component may be provided in an additional compartment within the developer container or in a separate container which may be identical such as a dual sachet or aerosol systems for example or different such as a bottle and tube system.

The consumer may mix the developer component and the dye component by any means. This may simply involve the use of a mixing bowl into which the components are dispensed and then mixed, preferably using a mixing means such as a tool. Alternatively, it may involve the addition of one of the components into the container of the other component (typically the dye component is added to the developer component), followed by manual shaking or mixing with a tool. Another system involves the perforation or displacement of a seal located between the separate compartments of the dye component and developer component within a single container or sachet followed by manual mixing within the container or in a separate and/or additional container.

The hair colouring kit may further comprise an applicator. The applicator may be a brush and bowl applicator. Alternatively, the applicator may be a nozzle which may be attached to one of the containers comprised in the kit in case the developer component, the dye component and the dilutant component are provided as separate containers in the kit or a separate applicator device such as a comb or a brush. Such combs and brushes can be adapted in order to achieve particular effects, whether it is quick and even coverage or root/hairline touch up, or highlights or streaks.

Alternatively, one of the containers may be provided with a comb attached to or instead of the dispensing nozzle whereby the product is dispensed through hollow tines and dispensing apertures located in the comb tines. The comb tines may be provided with single or multiple openings along the tines to improve product application and evenness especially root to tip. Product dispensation can be achieved by mechanical pressure applied to the container for example delaminating bottles or any of the mechanisms described hereinabove. The comb may be provided on the container such as to facilitate easy application and may be positioned vertically (so called verticomb) or at an angle to allow the consumer to access all areas.

The volume of developer component in the kit may be 10 mL to 120 mL, preferably 40 mL to 70 mL, more preferably 55 mL to 65 mL. The volume of dye component in the kit may be 10 mL to 120 mL, preferably 40 mL to 70 mL, more preferably 55 mL to 65 mL. The volume of dilutant component may be 10 mL to 120 mL, preferably 15 mL to 30 mL, more preferably 20 mL to 25 mL.

The components of the kit can be manufactured utilizing any one of the standard approaches, these include a) 'Oil in water' process, b) 'Phase Inversion' process and c) 'One-pot' process. For example, when using "oil in water" process, surfactants of the present invention are added to approximately 50% of total water amount of the compositions at about 90° C., homogenized for 15 to 30 min, then cooled to room temperature to form a premix; this premix is then mixed cold with remaining amounts of water, other optional components and/or oxidizing agent, thus forming the developer component and dye component of the above described colouring kit.

The kit may further comprise a set of instructions comprising instructing the user to colour its hair according to the method defined hereinbefore. The set of instruction may comprise:
  i) mixing the developer component with a dye component to obtain a non-diluted hair colouring composition;
  ii) applying a first portion of the non-diluted hair colouring composition obtained in step i) to the hair, preferably the hair roots and retaining a second portion of the non-diluted hair colouring composition obtained in step i);
  iii) mixing the second portion with the dilutant component at a mixing ratio of 4:1 to 1:2 to obtain a diluted hair colouring composition;
  iv) applying the diluted hair colouring composition to the hair, preferably the hair lengths and tips
  v) rinsing the hair.

The set of instructions may comprise any additional step which is disclosed hereinbefore in the method for colouring hair section of the application.

Viscosity Test Method:

The viscosity of a composition is measured using a TA Instruments AR 2000 Rheometer or equivalent device equipped with a Peltier plate and a 6 cm flat acrylic plate with cross hatchings. The instrument is calibrated according to the manufacturer's instructions and the Peltier plate is set at 25.0° C. The cone is raised to a position approximately 4.5 cm above the plate.

Immediately after the mixing, approximately 10 g of the mixture is transferred gently onto the centre of the Peltier plate using a spatula. The cone is lowered to obtain the specified gap between the tip of the cone and the upper surface of the Peltier plate. The gap setting is specified by the manufacturer of the cone and is typically approximately 1000 microns. The rheometer is programmed to operate in rotational mode with the shear stress ramped from 0.1 to 600 Pa over a period of 4 minutes, termination at 1000 reciprocal seconds. Rotation is initiated immediately after the specified gap is established. Viscosity data collected during the measurement period are shear stress (Pa) plotted as a function of shear rate ($s^{-1}$).

Experimental Data:
  1) Consumer Test Data 21 home hair colour kit users of standard level 3 oxidative hair colourant products were asked to use the dye, developer and dilutant component system of the present invention. The consumers were provided with their desired shade: 2 blondes (10/0 and 9/0) and 5 Browns (7/0. 7/7, 6/0, 5/0 and 5/43) and corresponding developer formulae 3 or 4 and diluter formula 1. The dye and developer compositions were mixed at a 1:1 ratio in a bowl. The consumer were instructed to apply 75% of the mixed using a brush and bowl application to their root hair line and leave on the roots for 20 minutes. The consumers were then instructed to mix the remaining mixed composition with the dilutant component (2:1 ratio) and apply the resulting composition to the remaining hair length and tips using their hands and to leave the composition on the hair for 10 min. The consumers were then instructed to rinse the product from their hair and apply a post colour conditioner component and dry and style as usual.

The consumers were then asked a number of questions regarding the colouring experience and outcome which is summarised below.

1. Considering everything about the test product, which of the following phrases best describes how you would rate it? (Select one)

| | | |
|---|---|---|
| The best hair color I have ever used or tried | 33% or 7 of 21 | |
| Slightly better than any other hair color I have ever used or tried | 52% or 11 of 21 | |
| The same as any other hair color I have ever used or tried | 10% or 2 of 21 | |
| Slightly worse than any other hair color I have ever used or tried | 0% | |
| The worst hair color I have ever used or tried | 5% or 1 of 21 | |

2. Now, thinking about the test product how you rate it for the following characteristics vs. your current hair color product?

Current retail products used by consumers in test were purchased from L'Oreal, Clairol, Revlon, Sally's and Wella.

| | Better | Same | Worse |
|---|---|---|---|
| Hair Color overall* | 81% or 17 of 21 | 14% or 3 of 21 | 5% of 1 of 21 |
| Your color for not being flat and block | 62% or 13 of 21 | 38% or 8 of 21 | 0% |
| Provides color full of depth and tones | 76% or 16 of 21 | 19 or 4 of 21 | 5% or 1 of 21 |
| Provides color with a rich blend of tones | 67% or 14 of 21 | 28% or 6 of 21 | 5% or 1 of 21 |

| Results Ratings | Base (21) |
|---|---|
| Hair Color & Conditioning attributes (1.0 = better, 0 = same) | |
| OA Hair Color | 0.8 |
| Not too flat and block | 0.6 |
| Full of depth and tones | 0.7 |
| Rich blend of tones | 0.6 |

2) Salon Test Data

Professional salon stylists treated 16 consumers to the following half head test.

Left side: invention
  Dye component (dye shades 9/0, 6/0 & 5/0) and developer component formula 3 or 4 mixed at 1:1 ratio and applied with brush & bowl application on the root hair for 30 minutes. Two thirds of the mixture was applied.
  Dilutant component (formula 2) added to remaining dye and developer mixture (one third remaining) and applied by stylist with hands on lengths and ends for 10 minutes
  Product rinsed from hair
  Post colour conditioner applied
  Dried and styled Right side: Retail application (prior art)
  Dye and developer composition mixed at 1:1 ratio and applied root to tip (brush and bowl) for 30 minutes
  Product rinsed from hair
  Post colour conditioner applied
  Dried and styled The colour results obtained were assessed by a professional. The stylist concluded that the colour was more brilliant, shinier and less intensive, which resulted in lighter colour in lengths and ends which removes the mono tonal appearance visible with the standard retail application. Visible strand to strand variation was also observed from the inventive compositions versus standard retail application.

Color Results

| Shade | Assessment |
|---|---|
| 9/0 | Noticeable more yellow less ash |
| | Slightly more Shine |
| | Slightly less intense (expected) |
| | Noticeable better Tone direction |
| | Noticeable more Brilliance |
| | Noticeable better Uniformity |
| 6/0 | Slightly more yellow less brown |
| | Slightly more Shine |
| | Slightly less intense (expected) |
| | Slightly better Tone direction |
| | Slightly more Brilliance |
| | Slightly better Uniformity |
| 5/0 | Noticeable more yellow less brown |
| | Slightly more Shine |
| | Slightly less intense (expected) |
| | Slightly better Tone direction |
| | Slightly more Brilliance |
| | Uniformity equal |

3) Viscosity Data

Different hair colouring compositions according to the present invention have been prepared.

Sample Preparation

Sample A0

15 g of dye component 7/0 were mixed with 15 g of developer component 1 in a can using a Speedmixer DAC400FVZ device for 40 s at 750 rpm. A small amount of the mixture was then removed from the can in order to collect viscosity data according to the viscosity test method.

Samples A1, B1 and C1

At t=0 s, 15 g of dye component 7/0 were mixed with 15 g of developer component 1 in a can using a Speedmixer DAC400FVZ device for 40 s at 750 rpm. At t=20 min, 15 g of the mixture were removed from the can, placed in a new can and 15 g of the dilutant component were added to the mixture in the new can. The resultant mixture was then mixed using a Speedmixer DAC400FVZ device for 40 s at 750 rpm. A small amount of the resultant mixture was then removed from the can in order to collect viscosity data according to the viscosity test method.

Samples A2, B2 and C2

At t=0 s, 15 g of dye component 7/0 were mixed with 15 g of developer component 1 in a can using a Speedmixer DAC400FVZ device for 40 s at 750 rpm. At t=20 min, 20 g of the mixture were removed from the can, placed in a new can and 10 g of the dilutant component were added to the mixture in the new can. The resultant mixture was then mixed using a Speedmixer DAC400FVZ device for 40 s at 750 rpm. A small amount of the resultant mixture was then removed from the can in order to collect viscosity data according to the viscosity test method.

Samples A3, B3 and C3

At t=0 s, 15 g of dye component 7/0 were mixed with 15 g of developer component 1 in a can using a Speedmixer DAC400FVZ device for 40 s at 750 rpm. At t=20 min, 10 g of the mixture were removed from the can, placed in a new can and 20 g of the dilutant component were added to the mixture in the new can. The resultant mixture was then mixed using a Speedmixer DAC400FVZ device for 40 s at 750 rpm. A small amount of the resultant mixture was then removed from the can in order to collect viscosity data according to the viscosity test method.

Dye component 7/0 and developer component 1 are disclosed hereinafter in the test formulation section of this application. The dilutant components which were used to prepare the different samples were selected from water, dilutant component 1, dilutant component 3 disclosed hereinafter in the test formulation section of the application and a shampoo dilutant component having the following formulation:

Shampoo Dilutant Component Formulation (Expressed in Percentages by Weight of the Total Composition):

The shampoo dilutant component comprises 6.0032% Sodium Laureth Sulfate, 6.0009% Sodium Lauryl Sulfate, 0.2505% Preservatives, 0.1344% Tetrasodium EDTA, 1.18% pH adjusters, 0.85% Cocamide MEA, 1.501% Stabilizers, 0.250% Guar Hydroxypropyltrimonium chloride, 0.999% Cocamidopropyl Betaine, 0.0300% Panthenol, 0.0300% Panthenyl Ethyl Ether, 0.20% Sodium Chloride, 0.84% Sodium xylenesulfonate, 0.65% Perfume, and up to 100% water.

Samples

| Sample name | Ratio[1] | SS[2] |
|---|---|---|
| A0 - dye component ("cpt") 7/0 + developer component 1 | | 167.57 |
| A1 - dye cpt 7/0 + developer cpt 1/dilutant cpt 1 | 1:1 | 60.27 |
| A2 - dye cpt 7/0 + developer cpt 1/dilutant cpt 1 | 2:1 | 74.25 |
| A3 - dye cpt 7/0 + developer cpt 1/dilutant cpt 1 | 1:2 | 48.07 |
| B1 - dye cpt 7/0 + developer cpt 1/water | 1:1 | 78.80 |
| B2 - dye cpt 7/0 + developer cpt 1/water | 2:1 | 135.23 |
| B3 - dye cpt 7/0 + developer cpt 1/water | 1:2 | 130.10 |
| C1 - dye cpt 7/0 + developer cpt 1/dilutant cpt 3 | 1:1 | 150.53 |
| C2 - dye cpt 7/0 + developer cpt 1/conditioner dilutant cpt 3 | 2:1 | 166.25 |
| C3 - dye cpt 7/0 + developer cpt 1/conditioner dilutant cpt 3 | 1:2 | 129.80 |
| D1 - dye cpt 7/0 + developer cpt 1/shampoo dilutant cpt | 1:1 | 13.50 |
| D2 - dye cpt 7/0 + developer cpt 1/shampoo dilutant cpt | 2:1 | 14.09 |
| D3 - dye cpt 7/0 + developer cpt 1/shampoo dilutant cpt | 1:2 | 17.97 |

[1]Mixing Ratio (dye component + developer component):dilutant component
[2]Shear Stress at 10 s$^{-1}$ Results As can be seen in the above table, when the dilutant component is a shampoo dilutant component which therefore comprises a high level of surfactant, substantial drop of viscosity is observed. For example for sample D2 a shear stress of 14.09 Pa at 10 s$^{-1}$ is observed whereas for sample A0, a shear stress of 167.57 Pa at 10 s$^{-1}$ is observed.

Consumer Test Data

Samples A0, A2, B2, C2 and D2 have been presented to a panel of 13 consumers placed from the left to the right in a randomized order. The consumers have been asked to assess the viscosity of the samples by indicating where on a 1-10 scale each product falls, where 1=thin and 10=thick.

Results

| | Sample name | | | | |
|---|---|---|---|---|---|
| | A0 | A2 | B2 | C2 | B2 |
| Consumer assessment | 9.5 | 6.0 | 6.1 | 9.5 | 2.2 |

The drop of viscosity which has been shown in the above viscosity data when the dilutant component is a shampoo dilutant component is confirmed by the panel of consumers. The viscosity hair colouring composition which is diluted with a shampoo dilutant component may therefore be too low to be applied to the hair lengths and tips with minimal to no dripping from the hair.

Test Formulations According to the Present Invention

In the following section all the values are expressed in percentages by weight of the total compositions.

| Dye component formulations | | | | | | | |
|---|---|---|---|---|---|---|---|
| Dye Component | 6/0 | 5/0 | 7/0 | 9/0 | 10/0 | 7/7 | 5/43 |
| Cetearyl alcohol and dicetyl phosphate and Ceteth-10 phosphate (Crodafos CES) | 9.0 | 9.0 | 9.0 | 9.0 | 9.0 | 9.0 | 9.0 |
| Cetearyl alcohol | 2.0 | 2.0 | 2.0 | 2.0 | 2.0 | 2.0 | 2.0 |
| Steareth-200 | 1.0 | 1.0 | 1.0 | 1.0 | 1.0 | 1.0 | 1.0 |
| Propylenglycol | 7.5 | 7.5 | 7.5 | 7.5 | 7.5 | 7.5 | 7.5 |
| EDTA disodium salt | 0.1 | 0.1 | 0.1 | 0.1 | 0.1 | 0.1 | 0.1 |
| Ascorbic acid | 0.3 | 0.3 | 0.3 | 0.3 | 0.3 | 0.3 | 0.3 |
| Sodium sulfit | 0.4 | 0.4 | 0.4 | 0.4 | 0.4 | 0.4 | 0.4 |
| Sodium sulfate | 1 | 1 | 1 | 0.5 | 0.5 | 1 | 1 |
| Ammonium sulfate | | | | | 0.5 | 0.5 | |
| Na3-ethlenediamine disuccinate | 3.35 | 3.35 | 3.35 | 3.35 | 3.35 | 3.35 | 3.35 |
| Toluene-2,5-diamine Sulfate | 0.935 | 1.309 | 0.69 | 0.182 | | 0.7 | 1.4 |
| 4-Amino phenol | 0.115 | 0.161 | 0.083 | 0.066 | | | 0.58 |
| Resorcinol | 0.455 | 0.637 | 0.337 | 0.11 | | 0.165 | 0.88 |
| 2-Methyl-recorcinol | | | | | | 0.165 | |
| 2.4-Diamino-phenoxyethanol HCL | 0.018 | 0.025 | 0.01 | | | | |
| m-Amminophenol | 0.105 | 0.145 | 0.074 | 0.045 | | 0.013 | 0.185 |
| 2-Methyl-5-hydroxyethylamino-phenol (Paox) | 0.025 | 0.035 | 0.02 | 0.003 | | 0.039 | 0.34 |
| 2-Amino-6-chloro-4-nitrophenol | | | | | | 0.008 | |
| Ammonium Hydroxide 25% | 0.7428 | 1.04 | 0.546 | 0.163 | | 0.51 | 1.28 |
| Ammonia 25% of buffer | | | | 0.48 | 0.48 | | |
| Ammonium Hydroxide 25% | 6.37 | 4 | 7.28 | 7.69 | 5.5 | 4.5 | 4.5 |
| Perfume | 0.25 | 0.25 | 0.25 | 0.25 | 0.25 | 0.25 | 0.25 |
| Water up to 100% | | | | | | | |

| Dye Component | 6/0[b] | 5/0[b] | 7/0[b] | 9/0[b] | 10/0[b] | 7/7[b] |
|---|---|---|---|---|---|---|
| Cetearyl alcohol and dicetyl phosphate and Ceteth-10 phosphate (Crodafos CES) | 9.0 | 9.0 | 9.0 | 9.0 | 9.0 | 9.0 |
| Cetearyl alcohol | 2.0 | 2.0 | 2.0 | 2.0 | 2.0 | 2.0 |
| Steareth-200 | 1.0 | 1.0 | 1.0 | 1.0 | 1.0 | 1.0 |
| Propylenglycol | 8.0 | 8.0 | 8.0 | 8.0 | 8.0 | 8.0 |
| EDTA disodium salt | 0.1 | 0.1 | 0.1 | 0.1 | 0.1 | 0.1 |
| Ascorbic acid | 0.3 | 0.3 | 0.3 | 0.3 | 0.3 | 0.3 |
| Sodium sulfite | 0.4 | 0.4 | 0.4 | 0.4 | 0.4 | 0.4 |
| Sodium sulfate | 1 | 1 | 1 | 0.5 | 0.5 | 1 |
| Ammonium sulfate | | | | | 0.5 | 0.5 |
| Na3-ethlenediamine disuccinate | 3.35 | 3.35 | 3.35 | 3.35 | 3.35 | 3.35 |
| Toluene-2,5-diamine Sulfate | 0.935 | 1.309 | 0.69 | 0.182 | | 0.7 |
| 4-Amino phenol | 0.115 | 0.161 | 0.083 | 0.066 | | |
| Resorcinol | 0.455 | 0.637 | 0.337 | 0.11 | | 0.165 |
| 2-Methyl-recorcinol | | | | | | 0.165 |
| 2.4-Diamino-phenoxyethanol HCL | 0.018 | 0.025 | 0.01 | | | |

-continued

| Dye Component | 6/0$^b$ | 5/0$^b$ | 7/0$^b$ | 9/0$^b$ | 10/0$^b$ | 7/7$^b$ |
|---|---|---|---|---|---|---|
| m-Amminophenol | 0.105 | 0.145 | 0.074 | 0.045 | | 0.013 |
| 4-Amino-2-hydroxytoluene (AHT) | | | | | | |
| 2-Methyl-5-hydroxyethylamino-phenol (Paox) | 0.025 | 0.035 | 0.02 | 0.003 | | 0.039 |
| 2-Amino-6-chloro-4-nitrophenol | | | | | | 0.008 |
| Sodium Hydroxide | 0.41 | 0.414 | 0.41 | 0.41 | 0.41 | 0.41 |
| Ammonia 25% of buffer | | | | 0.48 | 0.48 | |
| Xanthum gum | 0.15 | 0.15 | 0.15 | 0.15 | 0.15 | 0.15 |
| Ammonium Hydroxide 25% | 7.11 | 5.04 | 7.28 | 7.85 | 5.5 | 4.5 |
| Perfume | 0.25 | 0.25 | 0.25 | 0.25 | 0.25 | 0.25 |
| Water up to 100% | | | | | | |

Developer Component Formulations

| Developer component | 1 | 2 | 3 | 4 |
|---|---|---|---|---|
| Water Purified | Up to 100 | Up to 100 | Up to 100 | Up to 100 |
| Disodium EDTA. | 0.04 | 0.04 | | |
| Etidronic Acid | 0.08 | 0.08 | 0.01 | 0.01 |
| Aculyn 33 | 9.00 | 9.00 | | |
| Acrylates Steeareth-20 methacrylate copolymer | 0.10 | 0.10 | | |
| Hydrogen peroxide solution, 50% | 12.00 | 18.00 | 12.00 | 18.00 |
| Simethicone Emulsion | 0.01 | 0.01 | | |
| Cetearyl alcohol | | | 3.4 | 3.4 |
| Ceteareth-25 | | | 0.8 | 0.8 |
| Salicyclic acid | | | 0.1 | 0.1 |
| Disodium phosphate | | | 0.08 | 0.08 |

Dye formulation Shades 9/0 (9/0$^b$) and 10/0 are mixed together with developer components containing 9% hydrogen peroxide whereas dye formulation shades 5/0, 5/43, 6/0, 7/0 and 7/7 are mixed together with developer components containing 6% hydrogen peroxide.

Dilutant Component 1 Formulation (Expressed in Percentages by Weight of the Total Composition):
The dilutant component 1 comprises 1.8% Propylene glycol, 1.5% Hydroxycellulose, 2.0% Quaternium-80 (in 50% glycol), 1.25% Soytrimmonium chloride (60%), 0.5% PEG-40 hydrogenated castor oil, 0.4% Phenoxyethanol, 0.7% Cocoamidopropyl betaine, 0.002% Formic acid, 0.2% Perfume, 0.3% DMDM hydantoin, 0.1% Hydrolised sweet almond protein, 0.1% Disodium EDTA and up to 100% water.

Dilutant Component 2 Formulation (Expressed in Percentages by Weight of the Total Composition):
The dilutant component comprises 0.1% Guar hydroxypropyltrimonium chloride, 4.0% Cetrimonium chloride, 0.4% Phenoxyethanol, 0.3% Methyl paraben, 0.05% Titanium dioxide, 4.0% Cetearyl alcohol, 0.5% Fragrance, 0.1% Fruit extract and up to 100% water.

Dilutant Component 3 Formulation (after Colouring Conditioner Component 1) (Expressed in Percentages by Weight of the Total Composition):
The dilutant component 3 (after colouring conditioner component 1) comprises 2.0% Stearamidopropyl dimethylamine, 2.5% Cetyl alcohol, 4.5% Stearyl alcohol, 0.1% Ethylene diamine tetra acetic acid EDTA, 0.4333% Preservatives, 4.995% Amodimethicone, 0.005% Trimethylsiloxysilicate MQ resin, 0.64% L_Glutamic acid, 0.2250% Panthenyl ethyl ether, 0.045% Panthenol, 0.05% Safflower, 0.05% Coconut oil, 0.1% Hydrolyzed sweet almond, 0.005% Aloe Gel, 0.4% perfume and up to 100% water.

Dilutant component 3 may also be used as an after colouring conditioner.

After Colouring Conditioner Component 2 Formulation (Expressed in Percentages by Weight of the Total Composition):
The after colouring conditioner component 2 comprises 2.0% Stearamidopropyl dimethylamine, 2.5% Cetyl alcohol, 4.5% Stearyl alcohol, 0.1% Ethylene diamine tetra acetic acid EDTA, 0.4333% Preservatives, 6.993% Amodimethicone, 0.005% Trimethylsiloxysilicate MQ resin, 0.32% L_Glutamic acid, 0.2250% Panthenyl ethyl ether, 0.045% Panthenol, 0.05% Safflower, 0.05% Coconut oil, 0.1% Hydrolyzed sweet almond, 0.0070% Viscosity modifier, 0.4% perfume and up to 100% water.

After colouring conditioner component 1 is typically used after colouring of the hair with dye components 5/0, 5/43, 6/0, 7/0 and 7/7 whereas after colour conditioner component 2 is typically used after colouring of the hair with dye components 9/0 and 10/0.

The specific formulations and specific combinations of dye component and developer component and dilutant component formulations not used in the generation of the experimental data are used to illustrate the invention.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:
1. A method for colouring hair comprising the steps of:
  i) mixing a developer component with a dye component to obtain a non-diluted hair colouring composition, wherein the developer component comprises an oxidizing agent and the dye component comprises at least one oxidative dye precursor and/or an alkalising agent;
  ii) applying a first portion of the non-diluted hair colouring composition obtained in step i) to the hair and retaining a second portion of the non-diluted hair colouring composition obtained in step i);
  iii) mixing the second portion with a dilutant component comprising water and at least one active component selected from surfactants, conditioning agents, polymers and mixture thereof at a mixing ratio of about 4:1 to about 1:2 to obtain a diluted hair colouring composition;

iv) applying the diluted hair colouring composition to the hair;
v) rinsing the hair.

2. The method according to claim 1, wherein in step ii) the first portion of the non-diluted hair colouring composition is applied to the hair roots and in step iv) the diluted hair colouring composition is applied to the hair lengths and tips.

3. The method according to claim 1, wherein in step ii) from about 90 to about 10% by weight of the non-diluted hair colouring composition obtained in step i) is applied as a first portion to the hair.

4. The method according to claim 1, wherein:
the developer component comprises from about 1 to about 20% by weight of the oxidizing agent, and
the dye component comprises from about 0.01% to about 10% by weight of the oxidative dye precursor(s) and/or from about 0.1% to about 10% by weight of the alkalising agent, and
the dilutant component comprises up to about 99% by weight of water and up to about 25% by weight of at least one active component selected from surfactants, conditioning agents, polymers, and mixtures thereof.

5. The method according to claim 1, wherein the dilutant component comprises less than about 10% by weight of surfactant.

6. The method according to claim 1, wherein each of the non-diluted hair colouring composition and the diluted hair colouring composition has a viscosity which induces a shear stress of from about 20 to about 200 Pa at 10 s$^{-1}$ as measured according to the viscosity test method.

7. The method according to claim 1, wherein the non-diluted hair colouring composition has a viscosity which induces a shear stress of from about 60 to about 200 Pa at 10 s$^{-1}$ as measured according to the viscosity test method and the diluted hair colouring composition has a viscosity which induces a shear stress of from about 20 to about 180 Pa at 10 s$^{-1}$ as measured according to the viscosity test method.

8. The method according to claim 1, wherein the non-diluted hair colouring composition and the diluted hair colouring composition are applied to the hair with a brush and bowl applicator or a container to which a nozzle or a separate applicator device such as a comb or a brush is attached.

9. The method according to claim 1, wherein the non-diluted hair colouring composition and/or the diluted hair colouring composition comprises at least one gel network thickener system.

10. The method according to claim 1, wherein the developer component comprises a thickener selected from acrylates copolymer, hydrophobically modified acrylate copolymers and mixtures thereof.

11. The method according to claim 1, comprising the step of waiting for a time period $T_1$ which is performed between steps ii) and iii) and/or the step of waiting for a time period $T_2$ which is performed between steps iv) and v), wherein:

a. $0.15 < \left(\frac{T_2}{T_1 + T_2}\right) \times \left(1 - \frac{b}{a+b}\right) < 0.30$ or b. $0.55 < \left(\frac{T_2}{T_1 + T_2}\right) \times \left(1 - \frac{b}{a+b}\right) < 0.75$, wherein a and b are respectively the weight of the second portion of the non-diluted hair colouring composition and the weight of the dilutant component which are mixed together in step iii).

12. The method according to claim 1 comprising the step of waiting for a time period of from about 10 min to about 40 min, which is performed between steps ii) and iii) and the step of waiting for a time period of from about 5 min to about 20 min, which is performed between steps iv) and v).

13. The method according to claim 1, wherein step iii) is performed immediately after step ii) and wherein the method further comprises the step of waiting for a time period of from about 5 to about 40 min which is performed between steps iv) and v).

14. A hair colouring kit comprising a developer component comprising an oxidizing agent, a dye component comprising at least one oxidative dye precursor and/or an alkalising agent and a dilutant component comprising water and optionally at least one active component as defined in claim 1.

15. The hair colouring kit according to claim 14, wherein the kit further comprises a brush and bowl applicator.

16. The hair colouring kit according to claim 14, wherein the kit further comprises a shampoo for use in rinsing the hair after colouring and/or a conditioner component.

17. The hair colouring kit according to claim 14, wherein the kit further comprises a set of instructions comprising instructing the user to colour its hair.

18. A hair colouring composition comprising:
a developer component comprising an oxidizing agent, and
a dye component comprising at least one oxidative dye precursor and/or an alkalising agent, and a dilutant component comprising water and at least one active component selected from surfactants, conditioning agents, polymers and mixture thereof, wherein the hair colouring composition is obtainable by:
i) mixing the developer component and the dye component, wherein after mixing the developer component and the dye component, a first portion of the composition is applied to the hair and a second portion of the composition is retained, and
ii) mixing the second portion of the composition with the dilutant component at a mixing ratio of about 4:1 to about 1:2.

19. The hair colouring composition according to claim 18, wherein in step i) the first portion of the composition is applied to the hair roots.

* * * * *